(12) United States Patent
Shiina et al.

(10) Patent No.: US 8,552,215 B2
(45) Date of Patent: Oct. 8, 2013

(54) METHOD FOR PRODUCING OPTICALLY ACTIVE 2-HYDROXY ESTER AND NOVEL INTERMEDIATE COMPOUND

(75) Inventors: Isamu Shiina, Tokyo (JP); Kenya Nakata, Tokyo (JP)

(73) Assignee: Tokyo University of Science Educational Foundation Administrative Organization, Tokyo (JP)

( * ) Notice: Subject to any disclaimer, the term of this patent is extended or adjusted under 35 U.S.C. 154(b) by 83 days.

(21) Appl. No.: 13/255,465

(22) PCT Filed: Mar. 8, 2010

(86) PCT No.: PCT/JP2010/053789
§ 371 (c)(1),
(2), (4) Date: Sep. 8, 2011

(87) PCT Pub. No.: WO2010/104034
PCT Pub. Date: Sep. 16, 2010

(65) Prior Publication Data
US 2011/0319650 A1 Dec. 29, 2011

(30) Foreign Application Priority Data

Mar. 12, 2009 (JP) ................................ 2009-059850
Oct. 23, 2009 (JP) ................................ 2009-244060

(51) Int. Cl.
*C07C 69/013* (2006.01)
(52) U.S. Cl.
USPC .............................. 560/55; 548/151; 548/154
(58) Field of Classification Search
USPC ..................................... 560/55; 548/151, 154
See application file for complete search history.

(56) References Cited

U.S. PATENT DOCUMENTS 8,115,008 B2 * 2/2012 Shiina et al. .................. 548/151

FOREIGN PATENT DOCUMENTS

WO WO 2008/140074 A1 11/2008
WO WO 2009/113428 A1 9/2009

OTHER PUBLICATIONS

Birman et al; Organic Letters, 2007, 9(17), 3237-3240.*
Birman et al; Organic Letters, 2007, 9(1), 37-40.*
Xu et al; Tetrahedron, 65, 2009, 2232-2238.*
Zhou et al; Tetrahedron, 64, 2008, 6494-6499.*
Shinna et al; European Journal of Chemistry, 2008, 5887-5890.*
Birman, Vladimir B. and Li, Ximin, "Benzotetramisole: A Remarkably Enantioselective Acyl Transfer Catalyst", Organic Letters, vol. 8, No. 7, 2006, pp. 1351-1354.
Birman, Vladimir B. and Guo, Lel, "Kinetic Resolution of Propargylic Alcohols Catalyzed by Benzotetramisole", Organic Letters, vol. 8, No. 21, 2006, pp. 4859-4861.
Gröger, Harald, "Enzymatic Routes to Enantiomerically Pure Aromatic α-Hydroxy Carboxylic Acids: A Further Example for the Diversity of Biocatalysis", Adv. Synth. Catal. vol. 343, No. 6-7, 201, pp. 547-558, 2001.
Raghavan, Sadagopan et al., "A formal convergent synthesis of (+)-trans-solamin", Tetrahedron Letters, vol. 49, 2008, pp. 1601-1604.
Shiina, Isamu et al., "2,2-Disubstituted Propionic Anhydrides: Effective Coupling Reagents for the Kinetic Resolution of Secondary Benzylic Alcohols using BTM", Heterocycles, vol. 77, No. 2, 2009, pp. 801-810.
Shiina, Isamu and Nakata, Kenya, "The first asymmetric esterification of free carboxylic acids with racemic alcohols using benzoic anhydrides and tetramisole derivatives: an application to the kinetic resolution of secondary benzylic alcohols", Tetrahedron Letters, vol. 48, 2007, pp. 8314-8317.
Shiina, Isamu et al., "The First Total Synthesis of (−) and (+)-2-Hydroxy-24-oxooctacosanolide Using an Effective Lactonization", Organic Letters, vol. 8, No. 21, 2006, pp. 4955-4958.
International Search Report for PCT/JP2010/053789, mailed Apr. 6, 2010.

* cited by examiner

*Primary Examiner* — Johann R Richter
*Assistant Examiner* — Pancham Bakshi
(74) *Attorney, Agent, or Firm* — Hoffmann & Baron, LLP

(57) ABSTRACT

Disclosed is a method for producing an optically active 2-hydroxy ester, comprising selectively esterifying one enantiomer of a racemic 2-hydroxy ester in a solvent containing a catalyst such as tetramisole or benzotetramisole, and a carboxylic acid anhydride, or a carboxylic acid anhydride and a carboxylic acid. In particular, in the case where the solvent contains a carboxylic acid anhydride, but does not contain a carboxylic acid, as the carboxylic acid anhydride, a carboxylic acid anhydride containing a tertiary or quaternary carbon atom in the a-position is used. On the other hand, in the case where the solvent contains a carboxylic acid anhydride and a carboxylic acid, as the carboxylic acid, a carboxylic acid containing a tertiary or quaternary carbon atom in the a-position is used.

4 Claims, No Drawings

METHOD FOR PRODUCING OPTICALLY ACTIVE 2-HYDROXY ESTER AND NOVEL INTERMEDIATE COMPOUND

CROSS-REFERENCE TO RELATED APPLICATIONS

This application is the National Stage of International Application No. PCT/JP2010/053789, filed Mar. 8, 2010, which claims the benefit of Japanese Application Nos. 2009-059850, filed Mar. 12, 2009, and 2009-244060, filed Oct. 23, 2009, the entire contents of all of which are incorporated by reference herein.

FIELD OF THE INVENTION

The present invention relates to a method for producing an optically active 2-hydroxy ester, and a novel intermediate compound. More particularly, the present invention relates to a method for producing an optically active 2-hydroxy ester by carrying out kinetic optical resolution using a racemic 2-hydroxy ester as a substrate, and a novel intermediate compound that can be produced by the method.

BACKGROUND OF THE INVENTION

Optically active 2-hydroxy esters are one of useful organic molecules that can be widely used as medical drugs, pesticides, flavors, food additives, chemical products, optical materials, and the like. Therefore, development of an asymmetric synthesis method for rapidly and conveniently supplying these compounds is a very important study subject.

So far, a method for conveniently producing an optically active 2-hydroxy ester has been hardly reported. With respect to similar techniques, a method for producing an optically active 2-hydroxycarboxylic acid from a racemic 2-hydroxy ester has been reported in Nonpatent Document 1. In this Nonpatent Document 1, a method for producing an optically active 2-hydroxy-2-phenylacetic acid by hydrolyzing an ester moiety of a racemic 2-hydroxy-2-phenylacetic acid methyl ester with an enzyme, and the like are disclosed.

However, the substrate in the production method of Nonpatent Document 1 is limited to one having a phenyl group bonded to position 2; therefore, the method involves a problem of poor generality of the substrate. In addition, this production method does not directly produce an optically active 2-hydroxy ester, and thus lacks convenience for use in producing an optically active 2-hydroxy ester.

Patent Document 1: PCT International Publication No. 2008/140074
Nonpatent Document 1: Adv. Synth. Catal., 2001, 343, p. 547-558

SUMMARY OF THE INVENTION

Problems to be Solved by the Invention

It would be very advantageous if an optically active 2-hydroxy ester could be obtained by carrying out kinetic optical resolution using a racemic 2-hydroxy ester as a substrate. As only one example in the prior art, Example 10 of Patent Document 1 demonstrates that optically active benzyl 2-hydroxypropanoate is obtained by subjecting one enantiomer of racemic benzyl 2-hydroxypropanoate to selective esterification in a solvent containing benzotetramisole as an asymmetric catalyst, p-methoxybenzoic acid anhydride, and 3-phenylpropionic acid.

However, according to the production method disclosed in Patent Document 1, a reaction velocity ratio s is as low as 12. In an attempt to obtain an optically active 2-hydroxy ester having an enantiomeric excess of 99% in a yield of no less than 40% by kinetic optical resolution using a racemic 2-hydroxy ester as a substrate, a reaction velocity ratio s of no less than 25 is theoretically needed. Thus, a highly efficient production method has been desired which achieves a reaction velocity ratio s of greater than 25.

The present invention was made in view of such conventional problems, and an object of the invention is to provide a method for highly efficiently producing an optically active 2-hydroxy ester by carrying out kinetic optical resolution of a racemic 2-hydroxy ester as a substrate. In addition, another object of the present invention is to provide a novel intermediate compound that can be produced by the method.

Means for Solving the Problems

The present inventors thoroughly investigated in order to solve the foregoing problems. Consequently, it was found that the aforementioned problems could be solved by using a particular carboxylic acid anhydride or carboxylic acid when one enantiomer of a racemic 2-hydroxy ester is selectively esterified in a solvent containing a carboxylic acid anhydride, or a carboxylic acid anhydride and a carboxylic acid. Accordingly, the present invention was completed. More specifically, aspects of the present invention are as in the following.

A first aspect of the present invention provides a method for producing an optically active 2-hydroxy ester, the method including selectively esterifying one enantiomer of a racemic 2-hydroxy ester in a solvent containing a catalyst represented by any one of the following formulae (a) to (d), and a carboxylic acid anhydride, or a carboxylic acid anhydride and a carboxylic acid, the carboxylic acid anhydride being an anhydride of a carboxylic acid having a tertiary carbon atom or a quaternary carbon atom in the α-position, provided that the solvent contains a carboxylic acid anhydride but does not contain a carboxylic acid, whereas the carboxylic acid has a tertiary carbon atom or a quaternary carbon atom in the α-position, provided that the solvent contains a carboxylic acid anhydride and a carboxylic acid,

(a)

(b)

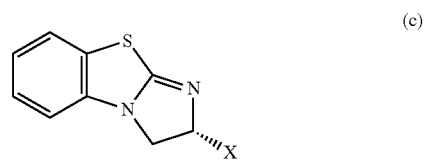

(c)

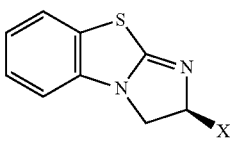

in the formulae (a) to (d), X represents any one of the following substituents:

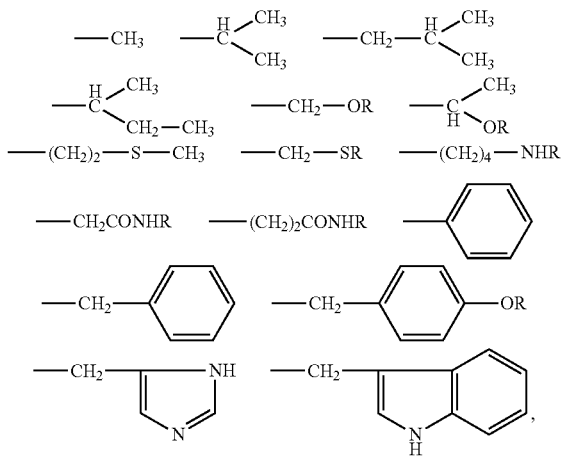

and R represents a protecting group.)

A second aspect of the present invention provides the method for producing an optically active 2-hydroxy ester according to the first aspect, wherein the one enantiomer of the racemic 2-hydroxy ester is selectively esterified in a solvent containing diphenylacetic acid anhydride as the carboxylic acid anhydride.

A third aspect of the present invention provides the method for producing an optically active 2-hydroxy ester according to the first aspect, wherein the one enantiomer of the racemic 2-hydroxy ester is selectively esterified in a solvent containing pivalic acid anhydride as the carboxylic acid anhydride, and diphenylacetic acid as the carboxylic acid.

A fourth aspect of the present invention provides the method for producing an optically active 2-hydroxy ester according to any one of the first to third aspects, wherein the solvent is a linear ether type solvent.

A fifth aspect of the present invention provides an intermediate compound represented by the following formula (e):

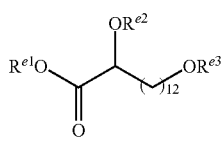

in the formula (e), $R^{e1}$ represents a monovalent organic group, $R^{e2}$ represents a hydrogen atom or a protecting group of a hydroxy group, and $R^{ea}$ represents a protecting group.

Effects of the Invention

According to the present invention, kinetic optical resolution carried out using a racemic 2-hydroxy ester as a substrate enables an optically active 2-hydroxy ester to be highly efficiently produced. In addition, a novel intermediate compound which can be produced with such a method may be provided.

DETAILED DESCRIPTION OF THE INVENTION

Method for Producing Optically Active 2-Hydroxy Ester

The method for producing an optically active 2-hydroxy ester according to the present invention includes selectively esterifying one enantiomer of a racemic 2-hydroxy ester in a solvent containing a particular catalyst, and a carboxylic acid anhydride, or a carboxylic acid anhydride and a carboxylic acid. By thus selectively esterifying one enantiomer, an optically active 2-hydroxy ester can be obtained as another enantiomer not esterified.

[Racemic 2-Hydroxy Ester]

The racemic 2-hydroxy ester used in the production method of the present invention is represented by the following formula (f):

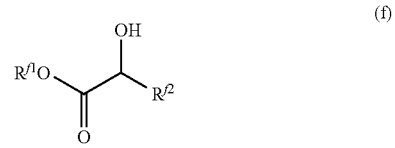

In the above formula (f), $R^{f1}$ and $R^{f2}$ each independently represent a monovalent organic group. The monovalent organic group is not particularly limited, and an arbitrary monovalent organic group may be used. Specific examples include an alkyl group, a cycloalkyl group, an alkenyl group, a cycloalkenyl group, an alkynyl group, an aryl group, a heteroaryl group, an arylalkyl group, and the like.

[Catalyst]

The catalyst used in the production method of the present invention is represented by any one of the following formulae (a) to (d).

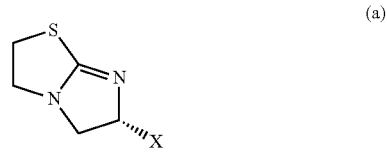

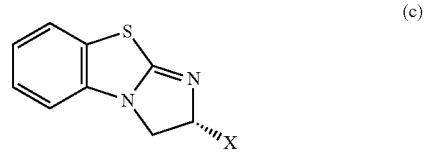

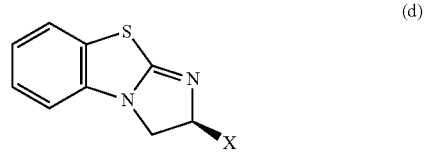

In the above formulae (a) to (d), X represents any one of the following substituents. R is a protecting group such as an alkyl group, an acyl group or a silyl group.

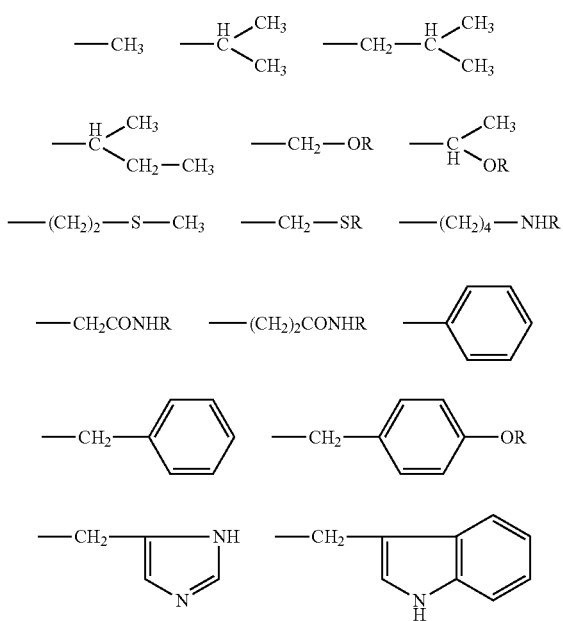

Of the catalysts represented by the above formulae (a) to (d), the catalysts each represented by the above formulae (a) and (b), wherein X is a phenyl group, are referred to as (+)-tetramisole and (−)-tetramisole, respectively. The catalysts each represented by the above formulae (c) and (d), wherein X is a phenyl group, are referred to as (+)-benzotetramisole, (−)-benzotetramisole, respectively. These catalysts can be either obtained as a commercially available product, or synthesized using an amino acid having the substituent represented by X as a side chain.

[Carboxylic Acid Anhydride]

When the carboxylic acid described later is not used in combination, the carboxylic acid anhydride used in the production method of the present invention serves as an acylating agent. The carboxylic acid anhydride which may be used in this case is an anhydride of a carboxylic acid having a tertiary carbon atom or a quaternary carbon atom in the α-position. Specific examples of the anhydride include those of isobutyric acid, pivalic acid, cyclohexane carboxylic acid, diphenylacetic acid or dinaphthylacetic acid.

On the other hand, when the carboxylic acid described later is used in combination, the carboxylic acid anhydride used in the production method of the present invention serves as a dehydrative condensation agent. Although the carboxylic acid anhydride in this case is not particularly limited, those obtained from benzoic acid, benzoic acid having an electron donating group such as an alkyl group, an alkoxy group, an amino group or an alkoxyalkyl group bonded to a phenyl group, or a polysubstituted carboxylic acid having a tertiary carbon atom or a quaternary carbon atom in the α-position are preferred, and those obtained from benzoic acid, a mono-, di- or tri-substituted benzoic acid to which an alkyl group or an alkoxy group having 1 to 3 carbon atoms is bonded, diphenylacetic acid, pivalic acid, 1-phenyl-1-cyclopentanecarboxylic acid, 2-methyl-2-phenylpropionic acid, or 2,2-diphenyl propionic acid are more preferred.

Among these, when the carboxylic acid described later is not used in combination, diphenylacetic acid anhydride is particularly preferred, whereas pivalic acid anhydride is particularly preferred when the carboxylic acid is used in combination. By using these carboxylic acid anhydrides, the intended optically active 2-hydroxy ester can be obtained at a high yield and with a high reaction velocity ratio s.

[Carboxylic Acid]

The carboxylic acid used in the production method of the present invention has a tertiary carbon atom or a quaternary carbon atom in the α-position. Examples of the carboxylic acid include isobutyric acid, pivalic acid, cyclohexane carboxylic acid, diphenylacetic acid, dinaphthylacetic acid, and the like. Of these, diphenylacetic acid is particularly preferred in light of achievement of a high enantiomeric excess ee and a high reaction velocity ratio s.

[Solvent]

The solvent used in the production method of the present invention is exemplified by: halogenated alkyls such as dichloromethane and chloroform; linear ethers such as diethyl ether, diisopropyl ether, tert-butylmethyl ether and cyclopentylmethyl ether; cyclic ethers such as tetrahydrofuran; aromatic compounds such as toluene, chlorobenzene, trifluoromethylbenzene (benzotrifluoride) and benzene; amides such as N,N-dimethylformamide and N-methylformamide; and the like. Of these, in light of attaining high yields and high reaction velocity ratios s, linear ether type solvents are particularly preferred.

[Reaction Conditions, etc.]

An optically active 2-hydroxy ester is produced by adding into a solvent a racemic 2-hydroxy ester, a catalyst, and a carboxylic acid anhydride, or a carboxylic acid anhydride and a carboxylic acid. Furthermore, in order to neutralize an acid derived from a carboxylic acid anhydride produced as the reaction proceeds, addition of a base into the reaction system is preferred. The base is preferably an organic base not having nucleophilicity (trimethyl amine, triethylamine, diisopropyl ethylamine).

The components may be added in any order into the solvent; however, sequentially adding the base, the catalyst, the racemic 2-hydroxy ester into a solvent containing a carboxylic acid anhydride, or a carboxylic acid anhydride and a carboxylic acid is preferred.

Although the amount of each component to be added is not particularly limited, with respect to 1 equivalent of the racemic 2-hydroxy ester, 0.5 to 1.2 equivalents of the carboxylic acid anhydride, 0.5 to 0.75 equivalents of the carboxylic acid and 1.0 to 2.4 equivalents of the base, and 1 to 10% by mole of the catalyst may be used.

The reaction temperature is preferably −23 to 30° C., and the reaction time is preferably 10 min to 48 hrs.

After the reaction was thus allowed, general method for isolation and purification may be used to isolate an optically active 2-hydroxy ester. Specifically, the target substance is extracted by liquid separation with an organic solvent such as dichloromethane or diethyl ether, and the organic layer is then concentrated, followed by purification on chromatography of the concentrate. Accordingly, the optically active 2-hydroxy ester and a diester can be each isolated separately.

Novel Intermediate Compound

The intermediate compound according to the present invention is represented by the following formula (e):

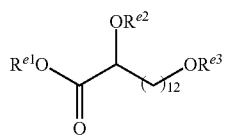

(e)

In the above formula (e): $R^{e1}$ represents a monovalent organic group; $R^{e2}$ represents a hydrogen atom or a protecting group of a hydroxy group; and $R^{e3}$ represents a protecting group such as a silyl group, a benzyl group, an acyl group or an acetal group. The monovalent organic group in $R^{e1}$ is not particularly limited, and those illustrated above in connection with $R^{f1}$ and the like may be used. Also, the protecting group in $R^{e2}$ is exemplified by an alkyl group, an acetyl group, a silyl group, and the like. Moreover, the silyl group in $R^{e3}$ is exemplified by a trimethyl silyl (TMS) group, a triethyl silyl (TES) group, a t-butyldimethyl silyl (TBS) group, a triisopropyl silyl (TIPS) group, a tert-butyldiphenyl silyl (TBDPS) group, and the like.

The intermediate compound is useful in producing for example, 2-hydroxy-24-oxooctacosanolide that is an insect repellent. One example of the method for producing 2-hydroxy-24-oxooctacosanolide is described later in Test Example 7.

EXAMPLES

Hereinafter, Examples of the present invention are explained, but the scope of the present invention is not limited to these Examples.

Test Example 1

Production of Optically Active 2-Hydroxy Ester Using Various Types of Carboxylic Acid

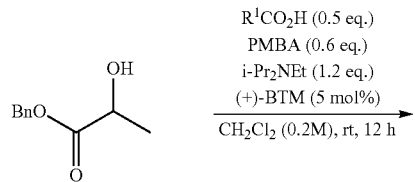

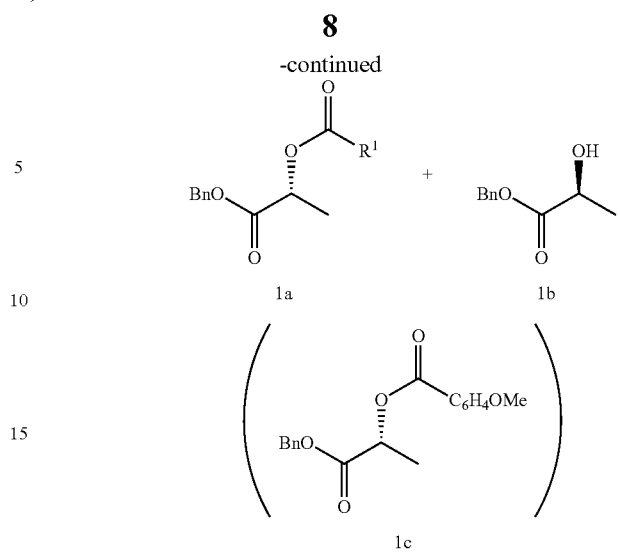

As shown in the above reaction scheme, to dichloromethane (0.2 M) containing 0.6 equivalents of p-methoxybenzoic acid anhydride (PMBA) and 0.5 equivalents of carboxylic acid were added 1.2 equivalents of diisopropyl ethylamine, 5% by mole of (+)-benzotetramisole (BTM), and a solution containing 1 equivalent of racemic benzyl lactate in dichloromethane at room temperature in this order, and this reaction mixture was stirred at room temperature for 12 hrs. Thereafter, the reaction was stopped with a saturated aqueous sodium bicarbonate solution. After the organic layer was fractionated, the aqueous layer was extracted with diethyl ether three to five times. It is to be noted that for Entries 6 and 7, the aqueous layer was extracted with dichloromethane. After the organic layer was mixed, the mixture was dried over anhydrous sodium sulfate. The solution was filtered and thereafter vacuum concentrated. Thus obtained mixture was fractionated on silica gel thin layer chromatography (developing solvent: hexane/ethyl acetate=3/1) to afford a corresponding diester and unreacted optically active benzyl lactate. The results are shown in Table 1.

The enantiomeric excess ee was determined by an HPLC analytical method on a chiral column. Further, the reaction velocity ratio s was calculated based on the formula of: s=[ln (1−C) (ee of 1−product)]/[ln(1−C) (ee of 1+product)], according to a method of Kagan et al, (Top. Stereochem., 1988, 18, p. 249-330).

TABLE 1

| No. | $R^1$ | Yield [%] of 1a[a] | 1a /1c[b] | Yield [%] of 1b[a] | ee (1a;1b) [%] | s |
|---|---|---|---|---|---|---|
| 1 | Ph(CH$_2$)$_2$ | 33 | 86/14 | 54 | 80;42 | 14 |
| 2 | p-TolCH$_2$ | 35 | 86/14 | 42 | 85;46 | 20 |
| 3 | i-Pr | 50 | 95/5 | 47 | 85;78 | 29 |
| 4 | c-Hex | 38 | 87/13 | 34 | 88;56 | 27 |
| 5 | Ph$_2$CH | 35 | 80/20 | 48 | 95;62 | 70 |
| 6 | (α-Np)$_2$CH | 8 | 84/16 | 86 | 94;6 | 35 |
| 7 | (β-Np)$_2$CH | 31 | 89/11 | 52 | 95;51 | 63 |

[a]Isolation yield
[b]Determined by $^1$H NMR

As is seen from Table 1, when a carboxylic acid having a secondary carbon atom in the α-position like a carboxylic acid in which $R^1$ is $Ph(CH_2)_2$ or $p\text{-TolCH}_2$ was used, the reaction velocity ratio s was no greater than 20 in either case, which was not satisfactory (Entries 1 and 2). On the other hand, when a more bulky carboxylic acid having a tertiary carbon atom in the α-position was used, the reaction velocity ratio s was as high as no less than 27. Accordingly, optically active benzyl lactate was successfully obtained with high efficiency (Entries 3 to 7). In particular, when diphenylacetic acid was used as the carboxylic acid, all of the yield, the enantiomeric excess ee, and the reaction velocity ratio s were very high (Entry 5).

Test Example 2

Production of Optically Active 2-Hydroxy Ester Using Various Types of Carboxylic Acid Anhydride

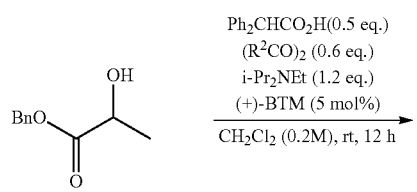

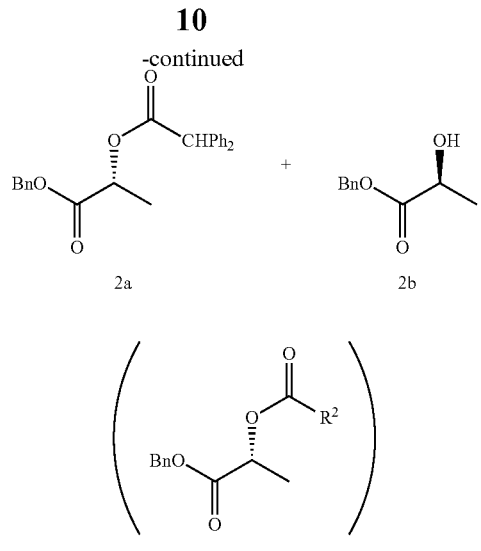

As shown in the above reaction scheme, to dichloromethane (0.2 M) containing 0.6 equivalents of carboxylic acid anhydride and 0.5 equivalents of diphenylacetic acid were added 1.2 equivalents of diisopropyl ethylamine, 5% by mole of (+)-benzotetramisole (BTM), and a solution containing 1 equivalent of racemic benzyl lactate in dichloromethane at room temperature in this order, and this reaction mixture was stirred at room temperature for 12 hrs. Thereafter, the reaction was stopped with a saturated aqueous sodium bicarbonate solution. After the organic layer was fractionated, the aqueous layer was extracted with diethyl ether three to five times. After the organic layer was mixed, the mixture was dried over anhydrous sodium sulfate. The solution was filtered and thereafter vacuum concentrated. Thus obtained mixture was fractionated on silica gel thin layer chromatography (developing solvent: hexane/ethyl acetate=3/1) to afford a corresponding diester and unreacted optically active benzyl lactate. The results are shown in Table 2.

TABLE 2

| No. | $R^2$ | Yield [%] of 2a[a] | 2a /2c[b] | Yield [%] of 2b[a] | ee (2a;2b) [%] | s |
|---|---|---|---|---|---|---|
| 8 | Ph | 46 | 87/13 | 43 | 92;84 | 64 |
| 9 | 4-MeOC$_6$H$_4$ | 35 | 80/20 | 48 | 95;62 | 70 |
| 10 | t-Bu | 44 | 98/2 | 55 | 94;68 | 62 |
| 11 | PhMe$_2$C | 27 | 98/2 | 43 | 95;75 | 92 |
| 12 | Ph$_2$MoC | 37 | >99/<1 | 44 | 96;62 | 87 |
| 13 | Ph$_3$C | 11 | >99/<1 | 75 | 97;12 | 72 |
| 14[c] | t-Bu | 44 | 98/2 | 55 | 97;82 | 146 |

[a]Isolation yield
[b]Determined by $^1$H NMR
[c]Diethyl ether used in place of dichloromethane As is seen from Table 2, Test Example 2 in which diphenylacetic acid was used as the carboxylic acid exhibited a very high reaction velocity ratio s of no less than 62 for any of the carboxylic acid anhydrides of Entries 8 to 14 used. Also, when a bulky carboxylic acid anhydride such as pivalic acid anhydride was used, the amount of the by-product (compound 2c) was small (Entries 10 to 14), and particularly, when pivalic acid anhydride was used, a high yield was attained (Entries 10 and 14). Furthermore, when diethyl ether was used in place of dichloromethane, a prominently high reaction velocity ratio s was attained (Entry 14).

Test Example 3

Production of Optically Active 2-Hydroxy Ester Using Various Types of Racemic 2-Hydroxy Ester (1)

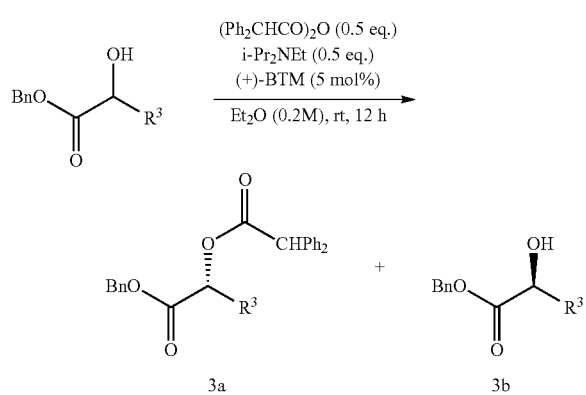

As shown in the above reaction scheme, to diethyl ether (0.2 M) containing 0.5 equivalents of diphenylacetic acid anhydride were added 0.5 equivalents of diisopropyl ethylamine, 5% by mole of (+)-benzotetramisole (BTM), and a solution containing 1 equivalent of racemic 2-hydroxy ester in diethyl ether at room temperature in this order, and this reaction mixture was stirred at room temperature for 12 hrs. Thereafter, the reaction was stopped with a saturated aqueous sodium bicarbonate solution. After the organic layer was fractionated, the aqueous layer was extracted with diethyl ether three to five times. After the organic layer was mixed, the mixture was dried over anhydrous sodium sulfate. The solution was filtered and thereafter vacuum concentrated. Thus obtained mixture was fractionated on silica gel thin layer chromatography (developing solvent: hexane/ethyl acetate=3/1) to afford a corresponding diester and an unreacted optically active 2-hydroxy ester. The results are shown in Table 3.

In addition, in a similar manner to that described above except that diethyl ether containing 0.6 equivalents of pivalic acid anhydride and 0.5 equivalents of diphenylacetic acid was used in place of the diethyl ether containing 0.5 equivalents of diphenylacetic acid anhydride, a diester and an unreacted optically active 2-hydroxy ester were obtained. The results thus obtained are shown in Table 3 presented in parentheses.

TABLE 3

| No. | $R^3$ | Yield [%] [a]<br>3a; 3b | ee [%]<br>3a; 3b | s |
|---|---|---|---|---|
| 15 | Me | 51; 49 | 97; 74 | 140 |
|    |    | (44; 55) | (97; 82) | (146) |
| 16 | Et | 48; 49 | 96; 86 | 152 |
|    |    | (46; 43) | (95; 94) | (126) |
| 17 | n-Pr | 45; 55 | 97; 84 | 149 |
|    |    | (50; 48) | (95; 97) | (171) |
| 18 | i-Pr | 40; 60 | 92; 66 | 46 |
|    |    | (46; 50) | (92; 73) | (53) |
| 19 | n-Bu | 45; 55 | 96; 86 | 125 |
|    |    | (47; 51) | (96; 88) | (128) |
| 20 | i-Bu | 46; 52 | 97; 87 | 167 |
|    |    | (45; 55) | (94; 97) | (140) |
| 21 | c-Hex | 38; 53 | 91; 63 | 42 |
|    |    | (43; 53) | (91; 75) | (47) |

TABLE 3-continued

| No. | $R^3$ | Yield [%] [a]<br>3a; 3b | ee [%]<br>3a; 3b | s |
|---|---|---|---|---|
| 22 | $(CH_2)_2Ph$ | 47; 53 | 96; 86 | 140 |
|    |    | (48; 47) | (96; 95) | (202) |
| 23 | $CH_2OTBS$ | 46; 54 | 94; 79 | 77 |
|    |    | (47; 50) | (93; 87) | (80) |
| 24 | $(CH_2)_2OTBS$ | 51; 49 | 93; 99 | 167 |
|    |    | (45; 52) | (96; 87) | (146) |
| 25 | $(CH_2)_3OTBS$ | 50; 43 | 95; 97 | 177 |
|    |    | (45; 59) | (97; 90) | (186) |
| 26 | $(CH_2)_{12}OTBS$ | 49; 49 | 95; 91 | 119 |
|    |    | (48; 48) | (96; 91) | (155) |

[a] Isolation yield

As is seen from Table 3, all cases of Entries 15 to 26 exhibited prominently high enantiomeric excess ee and reaction velocity ratio s for any of the 2-hydroxy esters used. In addition, achieving a high enantiomeric excess ee and a high reaction velocity ratio s was enabled also in the case in which a silyl group was bonded to the end of $R^3$ (Entries 23 to 26).

The production method and the physical properties of the optically active hydroxy esters and the diesters presented in Table 3 are shown below.

(Entry 17)

To diethyl ether (0.5 mL) containing diphenylacetic acid anhydride (45.2 mg, 0.111 mmol) were added diisopropyl ethylamine (19.4 μL, 0.111 mmol), (+)-benzotetramisole (2.8 mg, 0.0111 mmol), and a diethyl ether solution (0.6 mL) containing racemic benzyl 2-hydroxypentanoate (46.3 mg, 0.221 mmol) at room temperature in this order, and this reaction mixture was stirred at room temperature for 12 hrs. Thereafter, the reaction was stopped with a saturated aqueous sodium bicarbonate solution. After the organic layer was fractionated, the aqueous layer was extracted with diethyl ether five times. After the organic layer was mixed, the mixture was dried over anhydrous sodium sulfate. The solution was filtered and thereafter vacuum concentrated. Thus obtained mixture was fractionated on silica gel thin layer chromatography (developing solvent: hexane/ethyl acetate=3/1) to afford a corresponding diester (40.3 mg, 45%, 97% ee) and unreacted optically active benzyl 2-hydroxypentanoate (25.4 mg, 55%, 84% ee) as a colorless oily liquid (s=149).

Benzyl (S)-2-hydroxypentanoate

HPLC (CHIRALPAK AS-H, i-PrOH/hexane=1/9, flow rate=0.5 mL/min): $t_R$=15.0 min (98.6%), $t_R$=19.8 min (1.4%);
IR (neat): 3479, 1737, 1456, 1136, 751, 698 cm$^{-1}$;
$^1$H NMR (CDCl$_3$): δ7.41-7.32 (m, 5H, Ph), 5.21 (s, 2H, Bn), 4.23 (ddd, J=7.1, 5.0, 4.9 Hz, 1H, 2-H), 2.76 (d, J=5.0 Hz, 1H, OH), 1.82-1.73 (m, 1H, 3-H), 1.70-1.60 (m, 1H, 3-H), 1.53-1.34 (m, 2H, 4-H), 0.92 (t, J=7.5 Hz, 3H, 5-H);
$^{13}$C NMR (CDCl$_3$): δ174.8, 135.2, 128.63, 128.55, 128.4, 75.0, 67.3, 32.1, 18.8, 15.8;
HR MS: calcd for $C_{12}H_{16}O_3Na$ (M+Na$^+$) 231.0992. found 231.0980.

Benzyl (R)-2-(diphenylacetyloxy)pentanoate

HPLC (CHIRALCEL AD-H, i-PrOH/hexane=1/9, flow rate=0.5 mL/min): $t_R$=15.7 min (2.4%), $t_R$=21.3 min (97.6%);
IR (neat): 1742, 1496, 1454, 747, 697 cm$^{-1}$;
$^1$H NMR (CDCl$_3$): δ7.29-7.13 (m, 15H, Ph), 5.09 (d, J=12.0 Hz, 1H, Bn), 5.05 (d, J=12.0 Hz, 1H, Bn), 5.04 (s, 1H, 2'-H), 5.02 (dd, J=7.0, 6.0 Hz, 1H, 2-H), 1.73-1.67 (m, 2H, 3-H), 1.21 (tq, J=7.5, 7.5 Hz, 2H, 4-H), 0.75 (t, J=7.5 Hz, 3H, 5-H);

$^{13}$C NMR (CDCl$_3$): δ172.1, 170.0, 138.35, 138.26, 135.3, 128.71, 128.71, 128.57, 128.55, 128.4, 128.3, 128.2, 127.3, 127.2, 72.8, 66.9, 56.8, 33.0, 18.3, 13.4;

HR MS: calcd for C$_{26}$H$_{26}$O$_4$Na (M+Na$^+$) 425.1723. found 475.1703.

(Entry 15)

Benzyl (S)-lactate

HPLC (CHIRALCEL OD-H, i-PrOH/hexane=1/50, flow rate=1.0 mL/min): t$_R$=25.8 min (91.2%), t$_R$=28.9 min (8.8%);

IR (neat): 3457, 1738, 1498, 1456, 1045, 752, 698 cm$^{-1}$;

$^1$H NMR (CDCl$_3$): δ7.42-7.31 (m, 5H, Ph), 5.22 (s, 2H, Bn), 4.33 (dq, J=5.4, 6.9 Hz, 1H, 2-H), 2.81 (d, J=5.4 Hz, 1H, OH), 1.44 (d, J=6.9 Hz, 3H, 3-H);

$^{13}$C NMR (CDCl$_3$): δ175.5, 135.2, 128.6, 128.5, 128.2, 67.2, 66.8, 20.3;

HR MS: calcd for C$_{10}$H$_{12}$O$_3$Na (M+Na$^+$) 203.0679. found 203.0673.

Benzyl (R)-2-(diphenylacetyloxy)propanoate

HPLC (CHIRALCEL OJ-H, i-PrOH/hexane=2/3, flow rate=0.75 mL/min): t$_R$=40.2 min (1.7%), t$_R$=59.8 min (98.3%);

IR (neat): 1496, 1454, 747, 699 cm$^{-1}$;

$^1$H NMR (CDCl$_3$): δ7.41-7.20 (m, 15H, Ph), 5.19 (q, J=7.2 Hz, 1H, 2-H); 5.18 (d, J=12.0 Hz, 1H, Bn); 5.13 (d, J=12.0 Hz, 1H, Bn); 5.11 (s, 1H, 2'-H), 1.49 (d, J=7.2 Hz, 3H, 3-H);

$^{13}$C NMR (CDCl$_3$): δ171.9, 170.4, 138.3, 138.2, 135.2, 128.70, 128.66, 128.58, 128.56, 128.48, 128.3, 128.1, 127.3, 127.2, 69.3, 67.0, 56.6, 16.8;

HR MS: calcd for C$_{24}$H$_{22}$O$_4$Na (M+Na$^+$) 397.1410. found 397.1427.

(Entry 16)

Benzyl (S)-2-hydroxybutanoate

HPLC (CHIRALPAK AS-H, i-PrOH/hexane=1/9, flow rate=0.5 mL/min): t$_R$=15.6 min (96.7%), t$_R$=19.7 min (3.3%);

IR (neat): 3477, 1737, 1498, 1456, 1061, 752, 698 cm$^{-1}$;

$^1$H NMR (CDCl$_3$): δ7.40-7.32 (m, 5H, Ph), 5.24 (d, J=12.3 Hz, 1H, Bn), 5.20 (d, J=12.3 Hz, 1H, Bn), 4.20 (ddd, J=11.3, 7.3, 4.0 Hz, 1H, 2-H), 2.83 (d, J=5.5 Hz, 1H, OH), 1.86 (ddq, J=14.5, 4.0, 7.0 Hz, 1H, 3-H), 1.70 (ddq, J=14.5, 7.3, 7.5 Hz, 1H, 3-H), 0.95 (dd, J=7.5, 7.0 Hz, 3H, 4-H);

$^{13}$C NMR (CDCl$_3$): δ175.0, 135.2, 128.6, 128.5, 128.3, 71.4, 67.2, 27.4, 8.8;

HR MS: calcd for C$_{11}$H$_{14}$O$_3$Na (M+Na$^+$) 217.0835. found 217.0825.

Benzyl (R)-2-(diphenylacetyloxy)butanoate

HPLC (CHIRALCEL AD-H, i-PrOH/hexane=1/9, flow rate=0.5 mL/min): t$_R$=17.4 min (2.7%), t$_R$=20.9 min (97.3%);

IR (neat): 1736, 1496, 1454, 746, 699 cm$^{-1}$;

$^1$H NMR (CDCl$_3$): δ7.29-7.13 (m, 15H, Ph), 5.09 (d, J=12.0 Hz, 1H, Bn), 5.05 (d, J=12.0 Hz, 1H, Bn), 5.05 (s, 1H, 2'-H), 4.97 (dd, J=7.5, 5.0 Hz, 1H, 2-H), 1.85-1.71 (m, 2H, 3-H), 0.77 (t, J=7.5 Hz, 3H, 4-H);

$^{13}$C NMR (CDCl$_3$): δ172.1, 169.8, 138.36, 138.27, 135.26, 128.71, 128.71, 128.57, 128.55, 128.4, 128.3, 128.2, 127.3, 127.2, 74.0, 66.9, 56.8, 24.5, 9.4;

HR MS: calcd for C$_{25}$H$_{24}$O$_4$Na (M+Na$^+$) 411.1567. found 411.1559.

(Entry 18)

Benzyl (S)-2-hydroxy-3-methylbutanoate

HPLC (CHIRALCEL AS-H, i-PrOH/hexane=1/9, flow rate=0.5 mL/min): t$_R$=11.7 min (86.3%), t$_R$=17.0 min (13.7%);

IR (neat): 3508, 1735, 1498, 1456, 1030, 751, 698 cm$^{-1}$;

$^1$H NMR (CDCl$_3$): δ7.41-7.34 (m, 5H, Ph), 5.24 (d, J=12.3 Hz, 1H, Bn), 5.20 (d, J=12.3 Hz, 1H, Bn), 4.09 (dd, J=6.3, 3.5 Hz, 1H, 2-H), 2.71 (d, J=6.3 Hz, 1H, OH), 2.10 (dqq, J=3.5, 7.0, 7.0 Hz, 1H, 3-H), 1.01 (d, J=7.0 Hz, 3H, 4-H), 0.83 (d, J=7.0 Hz, 3H, 4-H);

$^{13}$C NMR (CDCl$_3$): δ175.3, 135.2, 128.6, 128.5, 128.3, 70.3, 67.2, 36.4, 18.0, 13.7;

HR MS: calcd for C$_{12}$H$_{16}$O$_3$Na (M+Na$^+$) 231.0992. found 231.0985.

Benzyl (S)-2-(diphenylacetyloxy)-3-methylbutanoate

HPLC (CHIRALCEL AD-H, i-PrOH/hexane=1/9, flow rate=0.5 mL/min): t$_R$=16.9 min (4.0%), t$_R$=21.8 min (96.0%);

IR (neat): 1739, 1496, 1454, 745, 698 cm$^{-1}$;

$^1$H NMR (CDCl$_3$): δ7.29-7.12 (m, 15H, Ph), 5.09 (d, J=12.3 Hz, 1H, Bn), 5.06 (s, 1H, 2'-H), 5.05 (d, J=12.3 Hz, 1H, Bn), 4.85 (d, J=4.5 Hz, 1H, 2-H), 2.11 (dqq, J=4.5, 7.0, 6.8 Hz, 1H, 3-H), 0.76 (d, J=7.0 Hz, 3H, 4-H), 0.75 (d, J=6.8 Hz, 3H, 4-H);

$^{13}$C NMR (CDCl$_3$): δ172.1, 169.3, 138.4, 138.3, 135.3, 128.8, 128.7, 128.6, 128.5, 128.4, 128.33, 128.29, 127.26, 127.16, 77.4, 66.9, 56.9, 30.2, 18.6, 17.0;

HR MS: calcd for C$_{26}$H$_{26}$O$_4$Na (M+Na$^+$) 425.1723. found 425.1732.

(Entry 19)

Benzyl (S)-2-hydroxyhexanoate

HPLC (CHIRALCEL AS-H, i-PrOH/hexane=1/9, flow rate=0.5 mL/min): t$_R$=12.9 min (93.8%), t$_R$=16.5 min (6.2%);

IR (neat): 3478, 1738, 1498, 1456, 1137, 751, 698 cm$^{-1}$;

$^1$H NMR (CDCl$_3$): δ7.42-7.32 (m, 5H, Ph), 5.23 (d, J=12.3 Hz, 1H, Bn), 5.20 (d, J=12.3 Hz, 1H, Bn), 4.27-4.18 (m, 1H, 2-H), 2.87 (d, J=5.5 Hz, 1H, OH), 1.87-1.74 (m, 1H, 3-H), 1.72-1.60 (m, 1H, 3-H), 1.48-1.25 (m, 4H, 4-H, 5-H), 0.88 (t, J=7.0 Hz, 3H, 6-H);

$^{13}$C NMR (CDCl$_3$): δ175.2, 135.2, 128.6, 128.5, 128.3, 70.5, 67.2, 34.0, 26.7, 22.3, 13.8;

HR MS: calcd for C$_{13}$H$_{18}$O$_3$Na (M+Na$^+$) 245.1148. found 245.1155.

Benzyl (R)-2-(diphenylacetyloxy)hexanoate

HPLC (CHIRALCEL AD-H, i-PrOH/hexane=1/50, flow rate=1.0 mL/min): t$_R$=19.7 min (2.2%), t$_R$=30.1 min (97.8%);

IR (neat): 1739, 1496, 1455, 736, 699 cm$^{-1}$;

$^1$H NMR (CDCl$_3$): δ7.32-7.16 (m, 15H, Ph), 5.12 (d, J=12.3 Hz, 1H, Bn), 5.08 (d, J=12.3 Hz, 1H, Bn), 5.07 (s, 1H, 2'-H), 5.04 (dd, J=7.0, 6.0 Hz, 1H, 2-H), 1.82-1.73 (m, 2H, 3-H), 1.23-1.10 (m, 4H, 4-H, 5-H), 0.78-0.71 (m, 3H, 6-H);

$^{13}$C NMR (CDCl$_3$): δ172.1, 170.0, 138.3, 138.2, 135.3, 128.71, 128.71, 128.6, 128.5, 128.4, 128.3, 128.2, 127.3, 127.2, 72.9, 66.9, 56.8, 30.7, 27.0, 22.0, 13.7;

HR MS: calcd for $C_{27}H_{28}O_4Na$ (M+Na$^+$) 439.1880. found 439.1886.
(Entry 20)

Benzyl (S)-2-hydroxy-4-methylpentanoate

HPLC (CHIRALCEL AS-H, i-PrOH/hexane=1/9, flow rate=0.5 mL/min): $t_R$=12.6 min (98.3%), $t_R$=18.0 min (1.7%);
IR (neat): 3474, 1737, 1498, 1456, 1090, 749, 698 cm$^{-1}$;
$^1$H NMR (CDCl$_3$): δ7.33-7.24 (m, 5H, Ph), 5.14 (d, J=12.0 Hz, 1H, Bn), 5.11 (d, J=12.0 Hz, 1H, Bn), 4.17 (ddd, J=8.5, 5.5, 5.0 Hz, 1H, 2-H), 2.64 (d, J=5.5 Hz, 1H, OH), 1.87-1.75 (m, 1H, 4-H), 1.55-1.46 (m, 2H, 3-H), 0.86 (d, J=7.0 Hz, 3H, 5-H), 0.85 (d, J=7.0 Hz, 3H, 5-H);
$^{13}$C NMR (CDCl$_3$): δ175.7, 135.2, 128.6, 128.5, 128.3, 69.1, 67.2, 43.4, 24.4, 23.2, 21.5;
HR MS: calcd for $C_{13}H_{18}O_3Na$ (M+Na$^+$) 245.1148. found 245.1156.

Benzyl (R)-2-(diphenylacetyloxy)-4-methylpentanoate

HPLC (CHIRALCEL AD-H, i-PrOH/hexane=1/9, flow rate=0.5 mL/min): $t_R$=14.2 min (2.8%), $t_R$=25.2 min (97.2%);
IR (neat): 1739, 1496, 1454, 739, 699 cm$^{-1}$;
$^1$H NMR (CDCl$_3$): δ7.29-7.13 (m, 15H, Ph), 5.10-5.00 (m, 4H, 2-H, 2'-H, Bn), 1.69 (ddd, J=14.0, 9.8, 4.5 Hz, 1H, 3-H), 1.58-1.41 (m, 3H, 3-H, 4-H), 0.75 (d, J=7.0 Hz, 3H, 5-H), 0.71 (d, J=6.5 Hz, 3H, 5-H);
$^{13}$C NMR (CDCl$_3$): δ172.1, 170.3, 138.3, 138.2, 135.2, 128.71, 128.69, 128.57, 128.54, 128.4, 128.3, 128.2, 127.3, 127.2, 71.7, 67.0, 56.8, 39.5, 24.5, 22.8, 21.3;
HR MS: calcd for $C_{27}H_{28}O_4Na$ (M+Na$^+$) 439.1880. found 439.1879.
(Entry 21)

Benzyl (S)-2-cyclohexyl-2-hydroxyacetate

HPLC (CHIRALCEL AS-H, i-PrOH/hexane=1/9, flow rate=0.5 mL/min): $t_R$=13.6 min (87.5%), $t_R$=20.3 min (12.5%);
IR (neat): 3504, 1735, 1498, 1452, 1114, 750, 697 cm$^{-1}$;
$^1$H NMR (CDCl$_3$): δ7.41-7.32 (m, 5H, Ph), 5.24 (d, J=12.0 Hz, 1H, Bn), 5.21 (d, J=12.0 Hz, 1H, Bn), 4.06 (d, J=3.5 Hz, 1H, 2-H), 2.69 (br s, 1H, OH), 1.81-1.57 (m, 5H, c-Hex), 1.43-1.03 (m, 6H, c-Hex);
$^{13}$C NMR (CDCl$_3$): δ174.7, 135.2, 128.6, 128.5, 128.3, 74.8, 67.2, 42.0, 29.0, 26.23, 26.18, 25.94, 25.89;
HR MS: calcd for $C_{15}H_{20}O_3Na$ (M+Na$^+$) 271.1305. found 271.1306.

Benzyl (R)-2-cyclohexyl-2-(diphenylacetyloxy)acetate

HPLC (CHIRALCEL AD-H, i-PrOH/hexane=1/9, flow rate=0.5 mL/min): $t_R$=18.6 min (4.6%), $t_R$=34.6 min (95.4%);
IR (neat): 1741, 1496, 1453, 747, 697 cm$^{-1}$;
$^1$H NMR (CDCl$_3$): δ7.27-7.13 (m, 15H, Ph), 5.09 (d, J=12.5 Hz, 1H, Bn), 5.06 (d, J=12.5 Hz, 1H, Bn), 5.05 (s, 1H, 2'-H), 4.84 (d, J=5.0 Hz, 1H, 2-H), 1.85-1.74 (m, 1H, c-Hex), 1.63-1.37 (m, 6H, c-Hex), 1.10-0.80 (m, 4H, c-Hex);
$^{13}$C NMR (CDCl$_3$): δ172.1, 169.3, 138.4, 138.3, 135.3, 128.78, 128.76, 128.54, 128.51, 128.4, 128.3, 128.2, 127.3, 127.1, 77.1, 66.8, 56.9, 39.5, 28.8, 27.3, 25.9, 25.8, 25.7;
HR MS: calcd for $C_{29}H_{30}O_4Na$ (M+Na$^+$) 465.2036. found 465.2031.
(Entry 22)

Benzyl (S)-2-hydroxy-4-phenylbutanoate

Mp: 58.9-59.6° C. (hexane);
HPLC (CHIRALCEL OD-H, i-PrOH/hexane=1/4, flow rate=0.5 mL/min): $t_R$=13.9 min (97.3%), $t_R$=19.1 min (2.7%);
IR (KBr): 3429, 1728, 1496, 1451, 1105, 752, 699 cm$^{-1}$;
$^1$H NMR (CDCl$_3$): δ7.32-7.23 (m, 5H, Ph), 7.22-7.16 (m, 2H, Ph), 7.13-7.05 (m, 3H, Ph), 5.11 (d, J=12.0 Hz, 1H, Bn), 5.08 (d, J=12.0 Hz, 1H, Bn), 4.16 (ddd, J=7.5, 5.5, 4.0 Hz, 1H, 2-H), 2.78 (d, J=5.5 Hz, 1H, OH), 2.72-2.56 (m, 2H, 4-H), 2.10-2.00 (m, 1H, 3-H), 1.93-1.83 (m, 1H, 3-H);
$^{13}$C NMR (CDCl$_3$): δ175.0, 141.1, 135.1, 128.7, 128.6, 128.5, 128.39, 128.38, 126.0, 69.7, 67.4, 35.9, 30.9;
HR MS: calcd for $C_{17}H_{18}O_3Na$ (M+Na$^+$) 293.1148. found 293.1158.

Benzyl (R)-2-(diphenylacetyloxy)-4-phenylbutanoate

Mp: 75.3-76.0° C. (hexane);
HPLC (CHIRALCEL AD-H, i-PrOH/hexane=1/9, flow rate=0.5 mL/min): $t_R$=22.0 min (1.8%), $t_R$=23.3 min (97.2%);
IR (KBr): 1734, 1496, 1455, 735, 697 cm$^{-1}$;
$^1$H NMR (CDCl$_3$): δ7.36-7.09 (m, 18H, Ph), 6.93-6.88 (m, 2H, Ph), 5.12 (d, J=12.0 Hz, 1H, Bn), 5.11 (s, 1H, 2'-H), 5.07 (d, J=12.0 Hz, 1H, Bn), 5.01 (dd, J=7.0, 6.0 Hz, 1H, 2-H), 2.54-2.42 (m, 2H, 4-H), 2.12-2.05 (m, 2H, 3-H);
$^{13}$C NMR (CDCl$_3$): δ171.9, 169.7, 140.1, 138.3, 138.2, 135.2, 128.77, 128.77, 128.66, 128.58, 128.48, 128.44, 128.41, 128.38, 128.3, 127.4, 127.3, 126.2, 72.1, 67.1, 56.8, 32.6, 31.0;
HR MS: calcd for $C_{31}H_{28}O_4Na$ (M+Na$^+$) 487.1880. found 487.1903.
(Entry 23)

Benzyl (S)-3-(tert-butyldimethylsiloxy)-2-hydroxypropanoate

HPLC (CHIRALCEL AD-H, i-PrOH/hexane=1/50, flow rate=1.0 mL/min): $t_R$=9.6 min (6.3%), $t_R$=10.4 min (93.7%);
IR (neat): 3506, 1748, 1462, 1123, 735, 697 cm$^{-1}$;
$^1$H NMR (CDCl$_3$): δ7.39-7.31 (m, 5H, Ph), 5.22 (s, 2H, Bn), 4.26 (dt, J=8.5, 3.0 Hz, 1H, 2-H), 3.96 (dd, J=10.3, 3.0 Hz, 1H, 3-H), 3.87 (dd, J=10.3, 3.0 Hz, 1H, 3-H), 3.07 (d, J=8.5 Hz, 1H, OH), 0.86 (s, 9H, TBS), 0.04 (s, 3H, TBS), 0.02 (s, 3H, TBS);
$^{13}$C NMR (CDCl$_3$): δ172.6, 135.3, 128.6, 128.4, 128.3, 72.0, 67.2, 65.0, 25.7, 18.2, −5.5, −5.6;
HR MS: calcd for $C_{16}H_{26}O_4SiNa$ (M+Na$^+$) 333.1493. found 333.1504.

Benzyl (R)-3-(tert-butyldimethylsiloxy)-2-(diphenylacetyloxy)propanoate

HPLC (CHIRALCEL AD-H, i-PrOH/hexane=1/50, flow rate=1.0 mL/min): $t_R$=11.2 min (96.5%), $t_R$=19.8 min (3.5%);
IR (neat): 1743, 1496, 1455, 746, 698 cm$^{-1}$;
$^1$H NMR (CDCl$_3$): δ7.36-7.20 (m, 15H, Ph), 5.23 (dd, J=5.0, 3.0 Hz, 1H, 2-H), 5.18 (d, J=12.0 Hz, 1H, Bn), 5.14 (d, J=12.0 Hz, 1H, Bn), 5.13 (s, 1H, 2'-H), 4.03 (dd, J=11.5, 5.0 Hz, 1H, 3-H), 3.91 (dd, J=11.5, 3.0 Hz, 1H, 3-H), 0.80 (s, 9H, TBS), −0.05 (s, 3H, TBS), −0.06 (s, 3H, TBS);

$^{13}$C NMR (CDCl$_3$): δ172.0, 167.8, 138.3, 138.1, 135.2, 128.8, 128.7, 128.6, 128.53, 128.46, 128.3, 128.2, 127.3, 127.2, 74.4, 67.1, 62.6, 56.8, 25.6, 18.1, −5.58, −5.58;

HR MS: calcd for C$_{30}$H$_{36}$O$_5$SiNa (M+Na$^+$) 527.2224. found 527.2245.

(Entry 24)

Benzyl (S)-4-(tert-butyldimethylsiloxy)-2-hydroxybutanoate

HPLC (CHIRALCEL AD-H, i-PrOH/hexane=1/50, flow rate=1.0 mL/min): t$_R$=10.0 min (6.3%), t$_R$=11.9 min (93.7%);
IR (neat): 3489, 1733, 1471, 1111, 735, 697 cm$^{-1}$;
$^1$H NMR (CDCl$_3$): δ7.39-7.31 (m, 5H, Ph), 5.23 (d, J=12.3 Hz, 1H, Bn), 5.19 (d, J=12.3 Hz, 1H, Bn), 4.40 (ddd, J=7.6, 5.5, 4.0 Hz, 1H, 2-H), 3.84-3.76 (m, 2H, 4-H), 3.31 (d, J=5.5 Hz, 1H, OH), 2.07 (dddd, J=14.2, 7.0, 5.5, 4.0 Hz, 1H, 3-H), 1.89 (dddd, J=14.2, 7.6, 6.0, 5.0 Hz, 1H, 3-H), 0.89 (s, 9H, TBS), 0.05 (s, 6H, TBS);
$^{13}$C NMR (CDCl$_3$): δ174.7, 135.4, 128.6, 128.4, 128.3, 69.0, 67.0, 59.9, 36.2, 25.9, 18.2, −5.5, −5.6;
HR MS: calcd for C$_{17}$H$_{28}$O$_4$SiNa (M+Na$^+$) 347.1649. found 347.1634.

Benzyl (R)-4-(tert-butyldimethylsiloxy)-2-(diphenylacetyloxy)butanoate

HPLC (CHIRALCEL AD-H, i-PrOH/hexane=1/50, flow rate=1.0 mL/min): t$_R$=9.8 min (98.1%), t$_R$=11.8 min (1.9%);
IR (neat): 1740, 1497, 1455, 747, 699 cm$^{-1}$;
$^1$H NMR (CDCl$_3$): δ7.46-7.31 (m, 15H, Ph), 5.36 (dd, J=9.0, 4.0 Hz, 1H, 2-H), 5.28 (d, J=12.3 Hz, 1H, Bn), 5.23 (d, J=12.3 Hz, 1H, Bn), 5.21 (s, 1H, 2'-H), 3.67 (ddd, J=10.3, 6.0, 4.5 Hz, 1H, 4-H), 3.60 (ddd, J=10.3, 8.0, 5.0 Hz, 1H, 4-H), 2.18 (dddd, J=14.1, 8.0, 6.0, 4.0 Hz, 1H, 3-H), 2.08 (dddd, J=14.1, 9.0, 5.0, 4.5 Hz, 1H, 3-H), 0.93 (s, 9H, TBS), 0.05 (s, 3H, TBS), 0.03 (s, 3H, TBS);
$^{13}$C NMR (CDCl$_3$): δ171.8, 170.1, 138.4, 138.2, 135.3, 128.74, 128.71, 128.6, 128.5, 128.4, 128.3, 128.1, 127.3, 127.2, 69.8, 66.9, 58.2, 56.8, 34.0, 25.8, 18.2, −5.5, −5.6;
HR MS: calcd for C$_{31}$H$_{38}$O$_5$SiNa (M+Na$^+$) 541.2381. found 541.2391.

(Entry 25)

Benzyl (S)-5-(tert-butyldimethylsiloxy)-2-hydroxypentanoate

HPLC (CHIRALPAK AS-H, i-PrOH/hexane=1/100, flow rate=1.0 mL/min): t$_R$=10.9 min (95.4%), t$_R$=17.0 min (4.6%);
IR (neat): 3470, 1732, 1471, 1102, 776, 697 cm$^{-1}$;
$^1$H NMR (CDCl$_3$): δ7.39-7.12 (m, 5H, Ph), 5.22 (d, J=12.5 Hz, 1H, Bn), 5.19 (d, J=12.5 Hz, 1H, Bn), 4.26 (dd, J=7.5, 4.0 Hz, 1H, 2-H), 3.67-3.59 (m, 2H, 5-H), 1.96-1.88 (m, 1H, 3-H), 1.80-1.55 (m, 4H, 3-H, 4-H, OH), 0.88 (s, 9H, TBS), 0.04 (s, 6H, TBS);
$^{13}$C NMR (CDCl$_3$): δ174.9, 135.3, 128.6, 128.5, 128.2, 70.4, 67.1, 62.8, 31.4, 28.2, 25.9, 18.3, −5.41;
HR MS: calcd for C$_{18}$H$_{33}$O$_4$SiNa (M+Na$^+$) 361.1806. found 361.1822.

Benzyl (R)-5-(tert-butyldimethylsiloxy)-2-(diphenylacetyloxy)pentanoate

HPLC (CHIRALPAK IC, i-PrOH/hexane=1/50, flow rate=1.0 mL/min): t$_R$=8.4 min (1.7%), t$_R$=9.5 min (98.3%);
IR (neat): 1741, 1496, 1455, 836, 698 cm$^{-1}$;
$^1$H NMR (CDCl$_3$): δ7.35-7.20 (m, 15H, Ph), 5.16 (d, J=12.5 Hz, 1H, Bn), 5.14 (d, J=12.5 Hz, 1H, Bn), 5.11 (s, 1H, 2'-H), 5.11 (dd, J=8.5, 5.0 Hz, 1H, 2-H), 3.51 (dd, J=6.0, 6.0 Hz, 2H, 5-H), 1.97-1.81 (m, 2H, 3-H), 1.50-1.41 (m, 2H, 4-H), 0.85 (s, 9H, TBS), −0.02 (s, 6H, TBS);
$^{13}$C NMR (CDCl$_3$): δ172.0, 170.0, 138.3, 138.2, 135.2, 128.7, 128.7, 128.6, 128.5, 128.4, 128.3, 128.1, 127.3, 127.2, 72.8, 66.9, 62.0, 56.8, 28.0, 27.7, 25.9, 18.2, −5.40;
HR MS: calcd for C$_{32}$H$_{40}$O$_5$SiNa (M+Na$^+$) 555.2537. found 555.2559.

(Entry 26)

Benzyl (S)-14-(tert-butyldimethylsiloxy)-2-hydroxytetradecanoate

HPLC (CHIRALPAK IC, i-PrOH/hexane=1/50, flow rate=0.5 mL/min): t$_R$=20.7 min (4.6%), t$_R$=22.9 min (95.4%);
IR (neat): 3472, 1736, 1462, 775, 697 cm$^{-1}$;
$^1$H NMR (CDCl$_3$): δ7.39-7.34 (m, 5H, Ph), 5.23 (d, J=12.0 Hz, 1H, Bn), 5.19 (d, J=12.0 Hz, 1H, Bn), 4.22 (dd, J=7.0, 4.5 Hz, 1H, 2-H), 3.60 (t, J=6.5 Hz, 2H, 14-H), 2.75 (br s, 1H, OH), 1.83-1.75 (m, 1H, 3-H), 1.69-1.60 (m, 1H, 3-H), 1.54-1.20 (m, 20H, 4-H, 5-H, 6-H, 7-H, 8-H, 9-H, 10-H, 11-H, 12-H, 13-H), 0.90 (s, 9H, TBS), 0.05 (s, 6H, TBS);
$^{13}$C NMR (CDCl$_3$): δ175.3, 135.2, 128.6, 128.5, 128.3, 70.5, 67.2, 63.3, 34.40, 34.38, 32.9, 29.62, 29.58, 29.56, 29.50, 29.4, 29.3, 26.0, 25.8, 24.6, 18.4, −5.27;
HR MS: calcd for C$_{27}$H$_{48}$O$_4$SiNa (M+Na$^+$) 487.3214. found 487.3230.

Benzyl (R)-14-(tert-butyldimethylsiloxy)-2-(diphenylacetyloxy)tetradecanoate

HPLC (CHIRALPAK AD-H, i-PrOH/hexane=1/100, flow rate=1.0 mL/min): t$_R$=11.2 min (98.0%), t$_R$=16.4 min (2.0%);
IR (neat): 1742, 1496, 1455, 836, 698 cm$^{-1}$;
$^1$H NMR (CDCl$_3$): δ7.24-7.10 (m, 15H, Ph), 5.05 (d, J=12.3 Hz, 1H, Bn), 5.01 (d, J=12.3 Hz, 1H, Bn), 5.00 (s, 1H, 2'-H), 4.97 (dd, J=7.0, 6.0 Hz, 1H, 2-H), 3.49 (t, J=6.5 Hz, 2H, 14-H), 1.71 (ddt, J=15.5, 7.0, 10.0 Hz, 1H, 3-H), 1.69 (ddt, J=15.5, 6.0, 9.0 Hz, 1H, 3-H), 1.40 (tt, J=7.0, 7.0 Hz, 2H, 13-H), 1.24-0.90 (m, 18H, 4-H, 5-H, 6-H, 7-H, 8-H, 9-H, 10-H, 11-H, 12-H), 0.79 (s, 9H, TBS), −0.06 (s, 6H, TBS);
$^{13}$C NMR (CDCl$_3$): δ172.1, 170.0, 138.3, 138.2, 135.3, 128.71, 128.70, 128.6, 128.5, 128.4, 128.3, 128.2, 127.3, 127.2, 72.9, 66.9, 63.3, 56.8, 32.9, 31.0, 29.62, 29.56, 29.55, 29.43, 29.39, 29.26, 28.9, 26.0, 25.8, 24.9, 18.4, −5.27;
HR MS: calcd for C$_{41}$H$_{58}$O$_5$SiNa (M+Na$^+$) 681.3946. found 681.3965.

Test Example 4

Production of Optically Active 2-Hydroxy Ester Using Various Types of Racemic 2-Hydroxy Ester (2)

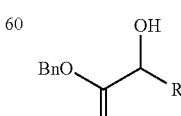
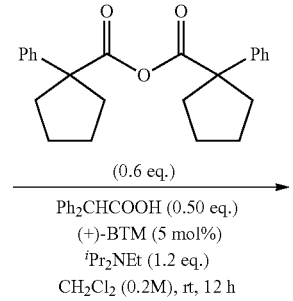
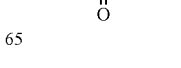

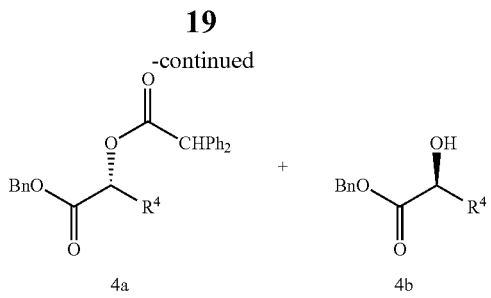

4a

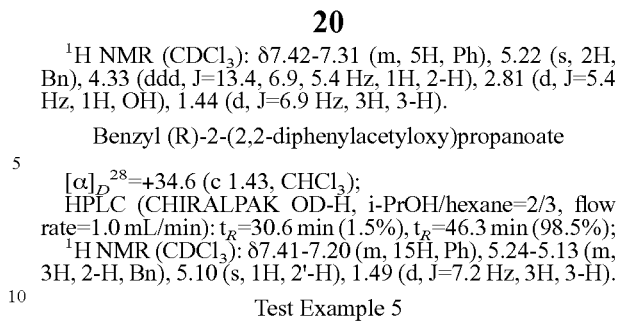

4b

As shown in the above reaction scheme, to a solution containing 0.50 equivalents of diphenylacetic acid and 0.60 equivalents of 1-phenyl-1-cyclopentanecarboxylic acid anhydride in dichloromethane were sequentially added 1.2 equivalents of diisopropyl ethylamine, 5% by mole of (+)-benzotetramisole ((+)-BTM), and the racemic 2-hydroxy ester at room temperature. This reaction mixture was then allowed to react at room temperature for 12 hrs, whereby a corresponding optically active ester and an unreacted 2-hydroxy ester were obtained. The results are shown in Table 4.

TABLE 4

| No. | R 4 | Yield [%] [a]<br>4a; 4b | ee [%]<br>4a; 4b | s |
|---|---|---|---|---|
| 27 | Me | 33; 58 | 97; 50 | 107 |
| 28 | Et | 31; 49 | 94; 52 | 58 |

[a] Isolation yield

As is seen from Table 4, also when 1-phenyl-1-cyclopentanecarboxylic acid anhydride and diphenylacetic acid were used in combination in place of diphenylacetic acid anhydride, prominently high enantiomeric excess ee and reaction velocity ratio s were attained (Entries 27 and 28).

The production method and the physical properties of the optically active hydroxy esters and the diesters presented in Table 4 are shown below.

(Entry 27)

To a solution containing 1-phenyl-1-cyclopentanecarboxylic acid anhydride (48.3 mg, 0.133 mmol) and diphenylacetic acid (23.6 mg, 0.111 mmol) in dichloromethane was added diisopropyl ethylamine (46.4 μL, 0.266 mmol) at room temperature. After this reaction mixture was stirred for 10 min, (+)-benzotetramisole (2.8 mg, 0.0111 mmol) and racemic benzyl lactate (35.7 μL, 0.222 mmol) were added thereto at room temperature. After this reaction mixture was stirred at room temperature for 12 hrs, saturated sodium bicarbonate water was added at room temperature to stop the reaction. After the organic layer was fractionated, the aqueous layer was extracted with diethyl ether five times. After the organic layer was mixed, the mixture was dried over anhydrous sodium sulfate. The solution was filtered and thereafter vacuum concentrated. Thus obtained mixture was fractionated on silica gel thin layer chromatography (developing solvent: hexane/ethyl acetate=3/1), and a highly polar fraction was fractionated again on silica gel thin layer chromatography (developing solvent: benzene/ethyl acetate=9/1) to afford a corresponding diester (23.0 mg, 58%, 50% ee) and unreacted optically active benzyl lactate. Moreover, the poorly polar fraction was also fractionated on silica gel thin layer chromatography (developing solvent: hexane/diethyl ether=5/1) to afford a corresponding diester (7.6 mg, 33%, 97% ee) and unreacted optically active benzyl lactate.

Benzyl (S)-lactate $[\alpha]_D^{28}$=−10.0 (c 1.10, acetone);
HPLC (CHIRALPAK OD-H, i-PrOH/hexane=1/50, flow rate=1.0 mL/min): $t_R$=16.7 min (75.2%), $t_R$=18.7 min (24.8%);

$^1$H NMR (CDCl$_3$): δ7.42-7.31 (m, 5H, Ph), 5.22 (s, 2H, Bn), 4.33 (ddd, J=13.4, 6.9, 5.4 Hz, 1H, 2-H), 2.81 (d, J=5.4 Hz, 1H, OH), 1.44 (d, J=6.9 Hz, 3H, 3-H).

Benzyl (R)-2-(2,2-diphenylacetyloxy)propanoate $[\alpha]_D^{28}$=+34.6 (c 1.43, CHCl$_3$);
HPLC (CHIRALPAK OD-H, i-PrOH/hexane=2/3, flow rate=1.0 mL/min): $t_R$=30.6 min (1.5%), $t_R$=46.3 min (98.5%);
$^1$H NMR (CDCl$_3$): δ7.41-7.20 (m, 15H, Ph), 5.24-5.13 (m, 3H, 2-H, Bn), 5.10 (s, 1H, 2'-H), 1.49 (d, J=7.2 Hz, 3H, 3-H).

Test Example 5

Production of Optically Active 2-Hydroxy Ester Using Various Types of Racemic 2-Hydroxy Ester (3)

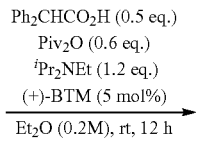

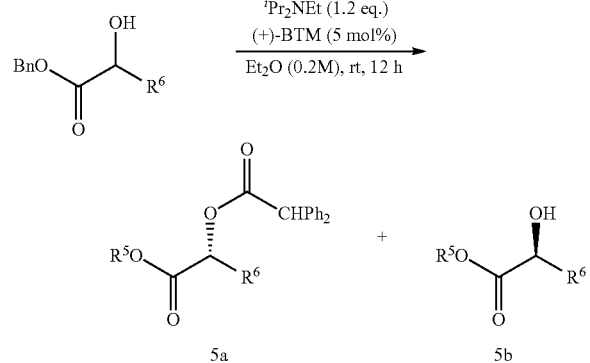

5a

5b

As shown in the above reaction scheme, to diethyl ether (0.2 M) containing 0.6 equivalents of pivalic acid anhydride and 0.5 equivalents of diphenylacetic acid were added 1.2 equivalents of diisopropyl ethylamine, 5% by mole of (+)-benzotetramisole (BTM), and a solution containing 1 equivalent of a racemic 2-hydroxy ester in diethyl ether at room temperature in this order, and this reaction mixture was stirred at room temperature for 12 hrs. Thereafter, the reaction was stopped with a saturated aqueous sodium bicarbonate solution. After the organic layer was fractionated, the aqueous layer was extracted with diethyl ether three to five times. After the organic layers were admixed, the mixture was dried over anhydrous sodium sulfate. The solution was filtered and thereafter vacuum concentrated. Thus obtained mixture was fractionated on silica gel thin layer chromatography (developing solvent: hexane/ethyl acetate=3/1) to afford a corresponding diester and unreacted optically active 2-hydroxy ester. The results are shown in Table 5.

TABLE 5

| No. | R$^5$ | R$^6$ | Yield [%] [a]<br>5a; 5b | ee [%]<br>5a; 5b | s |
|---|---|---|---|---|---|
| 29 | Et | n-Pr | 47; 47 | 97; 89 | 217 |
| 30 | Me | Me | 47; 23 | 97; 68 | 119 |

[a] Isolation yield

As is seen from Table 5, prominently high enantiomeric excess ee and reaction velocity ratio s were exhibited also when a material other than the benzyl ester was used (Entries 29 and 30).

The physical properties of the optically active hydroxy esters and the diesters in Table 5 are shown below.

(Entry 29)

Ethyl (S)-2-hydroxypentanoate $^1$H NMR (CDCl$_3$): δ4.19 (dq, J=14.0, 7.0 Hz, 1H, Eta), 4.18 (dq, J=14.0, 7.5 Hz, 1H, Eta), 2.96 (br d, J=3.5 Hz, 1H, OH), 1.75-1.65 (m, 1H, 3-H), 1.62-1.52 (m, 1H, 3-H), 1.48-1.30 (m, 2H, 4-H), 1.24 (dd, J=7.5, 7.0 Hz, 3H, Eta), 0.89 (t, J=7.3 Hz, 3H, 5-H);

$^{13}$C NMR (CDCl$_3$): δ175.3, 70.2, 61.4, 36.4, 17.9, 14.1, 13.6.

Ethyl (R)-2-(diphenylacetyloxy)pentanoate

HPLC (CHIRALCEL AD-H, i-PrOH/hexane=1/50, flow rate=1.0 mL/min): t$_R$=15.0 min (1.4%), t$_R$=17.5 min (98.6%);

IR (neat): 1745, 1496, 1454, 745, 701 cm$^{-1}$;

$^1$H NMR (CDCl$_3$): δ7.33-7.17 (m, 10H, Ph), 5.08 (s, 1H, 2'-H), 4.98 (dd, J=7.0, 6.0 Hz, 1H, 2-H), 4.12 (dq, J=14.0, 7.5 Hz, 3H, Eta), 4.11 (dq, J=14.0, 7.0 Hz, 3H, Eta), 1.78-1.71 (m, 2H, 3-H), 1.32-1.28 (m, 2H, 4-H), 1.16 (dd, J=7.5, 7.0 Hz, 3H, Eta), 0.81 (t, J=7.5 Hz, 3H, 5-H);

$^{13}$C NMR (CDCl$_3$): δ172.1, 170.1, 138.4, 138.3, 128.7, 128.6, 128.4, 127.3, 127.2, 120.4, 72.9, 61.2, 56.8, 33.0, 18.3, 14.0, 13.5;

HR MS: calcd for C$_{21}$H$_{24}$O$_4$Na (M+Na$^+$) 363.1567. found 363.1569.

(Entry 30)

Methyl (S)-lactate $^1$H NMR (CDCl$_3$): δ4.24 (q, J=7.0 Hz, 1H, 2-H), 3.72 (s, 3H, MeO), 3.16 (br s, 1H, OH), 1.36 (d, J=7.0 Hz, 3H, 3-H);

$^{13}$C NMR (CDCl$_3$): δ176.0, 66.6, 52.3, 20.2.

Methyl (R)-2-(diphenylacetyloxy)propanoate

HPLC (CHIRALCEL AD-H, i-PrOH/hexane=1/50, flow rate=0.75 mL/min): t$_R$=16.4 min (98.3%), t$_R$=19.7 min (1.7%);

IR (neat): 1744, 1496, 1454, 748, 699 cm$^{-1}$;

$^1$H NMR (CDCl$_3$): δ7.28-7.20 (m, 8H, Ph), 7.19-7.13 (m, 2H, Ph), 5.07 (q, J=7.0 Hz, 1H, 2-H), 5.03 (s, 1H, 2'-H), 3.60 (s, 3H, MeO), 1.37 (d, J=7.0 Hz, 3H, 3-H);

$^{13}$C NMR (CDCl$_3$): δ171.9, 170.9, 138.3, 138.2, 128.7, 128.63, 128.55, 128.4, 127.3, 127.2, 69.2, 56.6, 52.2, 16.8;

HR MS: calcd for C$_{18}$H$_{18}$O$_4$Na (M+Na$^+$) 321.1097. found 321.1091.

Test Example 6

Production of Optically Active 2-Hydroxy Ester Using Various Types of Solvent

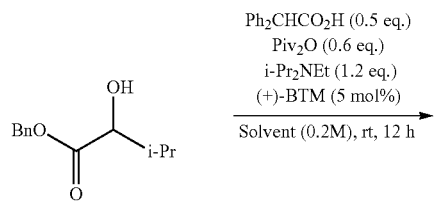

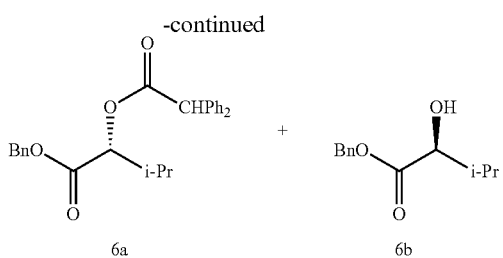

As shown in the above reaction scheme, to a solvent (0.2 M) containing 0.6 equivalents of pivalic acid anhydride and 0.5 equivalents of diphenylacetic acid were added to 1.2 equivalents of diisopropyl ethylamine, 5% by mole of (+)-benzotetramisole (BTM), and a solvent containing 1 equivalent of racemic benzyl 2-hydroxy-3-methylbutanoate at room temperature in this order, and this reaction mixture was stirred at room temperature for 12 hrs. Thereafter, the reaction was stopped with a saturated aqueous sodium bicarbonate solution. After the organic layer was fractionated, the aqueous layer was extracted with diethyl ether three to five times. After the organic layer was mixed, the mixture was dried over anhydrous sodium sulfate. The solution was filtered and thereafter vacuum concentrated. Thus obtained mixture was fractionated on silica gel thin layer chromatography (developing solvent: hexane/ethyl acetate=3/1) to afford a corresponding diester and unreacted optically active benzyl 2-hydroxy-3-methylbutanoate. The results are shown in Table 6.

TABLE 6

| No. | solvent | Yield [%] [a]<br>6a; 6b | ee [%]<br>6a; 6b | s |
|---|---|---|---|---|
| 31 | Et$_2$O | 46; 50 | 92; 73 | 53 |
| 32 | i-Pr$_2$O | 44; 54 | 92; 77 | 57 |
| 33 | MTBE [b] | 40; 54 | 93; 69 | 52 |
| 34 | CPME [c] | 36; 58 | 93; 53 | 50 |
| 35 | THF [d] | 38; 61 | 90; 57 | 33 |
| 36 | DMF [e] | 10; 82 | 92; 22 | 28 |

[a] Isolation yield
[b] methyl tert-butyl ether
[c] cyclopentyl methyl ether
[d] tetrahydrofuran
[e] N,N-dimethylformamide As is seen from Table 6, all cases of Entries 31 to 36 exhibited favorable enantiomeric excess ee and reaction velocity ratio s for any of the solvents used, and in particular, the reaction velocity ratio s was as high as no less than 50 when the linear ether type solvent was used (Entries 31 to 34).

Test Example 7

Production of Insect Repellent Using Optically Active Hydroxy Ester

Benzyl (S)-14-(tert-butyldimethylsiloxy)-2-hydroxytetradecanoate obtained in Entry 26 of the aforementioned Test Example 3 is useful as, for example, an intermediate compound for producing 2-hydroxy-24-oxooctacosanolide that is an insect repellent. Accordingly, one example of the production method is shown in the following.

(Step 1)

To a solution of benzyl (S)-14-(tert-butyldimethylsiloxy)-2-hydroxytetradecanoate (46.5 mg, 0.100 mmol) in methylene chloride (0.5 mL) were added a solution of 4-methoxybenzyl 2,2,2-trichloroacetimidate (62.2 mg, 0.220 mmol) in methylene chloride (0.5 mL), and (±)-camphor sulfonic acid (2.3 mg, 0.010 mmol), and the mixture was stirred at room temperature for 16 hrs. The reaction system was diluted in hexane, filtered through Celite, and vacuum concentrated to obtain a crude product. Thus obtained crude product was purified on thin layer chromatography (developing solvent: benzene) to afford a compound A (19.5 mg, 33%) represented by the following formula as a colorless oily liquid. The physical properties were as in the following.

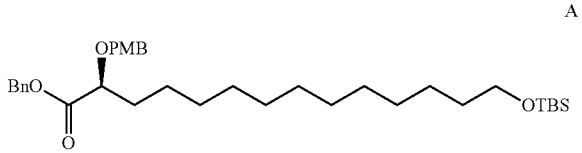

A

IR (neat): 1749, 1613, 1514, 835, 775 cm$^{-1}$;
$^1$H NMR (CDCl$_3$): δ7.39-7.31 (m, 5H, Ph), 7.23 (dt, J=8.5, 2.5 Hz, 2H, PMP), 6.85 (dt, J=8.5, 2.5 Hz, 2H, PMP), 5.21 (d, J=12.3 Hz, 1H, Bn), 5.16 (d, J=12.3 Hz, 1H, Bn), 4.61 (d, J=11.3 Hz, 1H, PMB), 4.33 (d, J=11.3 Hz, 1H, PMB), 3.94 (dd, J=7.0, 6.5 Hz, 1H, 2-H), 3.80 (s, 3H, OMe), 3.60 (t, J=6.8 Hz, 2H, 14-H), 1.77-1.69 (m, 2H, 3-H), 1.51 (tt, J=7.0, 7.0 Hz, 2H, 13-H), 1.42-1.17 (m, 18H, 4-H, 5-H, 6-H, 7-H, 8-H, 9-H, 10-H, 11-H, 12-H), 0.90 (s, 9H, TBS), 0.05 (s, 6H, TBS);
$^{13}$C NMR (CDCl$_3$): δ173.0, 159.3, 135.7, 129.7, 129.63, 129.56, 128.32, 128.30, 113.7, 77.7, 71.9, 66.4, 63.3, 55.2, 33.0, 32.9, 29.65, 29.60, 29.60, 29.54, 29.46, 29.42, 29.2, 26.0, 25.8, 25.2, 18.4, −5.26;
HR MS: calcd for C$_{35}$H$_{56}$O$_5$SiNa (M+Na$^+$) 607.3789. found 607.3789.

(Step 2)

A solution of the compound A (19.5 mg, 33.3 μmol) in methylene chloride (0.67 mL) was cooled to 0° C., and thereto was added hydrogenated diisobutyl aluminum (1.0 M hexane solution, 0.10 mL, 0.100 mmol). The mixture was stirred for 5 min. To the reaction system was added a saturated aqueous potassium sodium tartrate solution to stop the reaction. The mixture was subjected to liquid separation by adding methylene chloride, and extraction from the aqueous layer was repeated three times with methylene chloride. The extracted layer was filtrated, and vacuum concentrated to give a crude product. Thus obtained crude product was purified on thin layer chromatography (developing solvent: hexane/ethyl acetate=3/1) to afford a compound B (12.9 mg, 81%) represented by the following formula as a colorless oily liquid. The physical properties were as in the following.

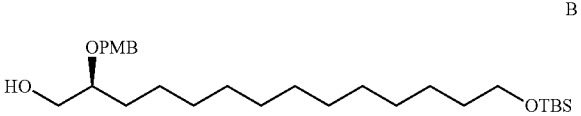

B

IR (neat): 3438, 1613, 1514, 1100, 836, 775 cm$^{-1}$;
$^1$H NMR (CDCl$_3$): δ7.27 (dt, J=8.5, 2.0 Hz, 2H, PMP), 6.88 (dt, J=8.5, 2.0 Hz, 2H, PMP), 4.56 (d, J=11.3 Hz, 1H, PMB), 4.46 (d, J=11.3 Hz, 1H, PMB), 3.80 (s, 3H, OMe), 3.69-3.65 (m, 1H, 2-H), 3.60 (t, J=6.5 Hz, 2H, 14H), 3.53-3.46 (m, 2H, 1-H), 1.65-1.43 (m, 4H, 3-H, 13-H), 1.37-1.24 (m, 19H, 4-H, 5-H, 6-H, 7-H, 8-H, 9-H, 10-H, 11-H, 12-H, OH), 0.89 (s, 9H, TBS), 0.05 (s, 6H, TBS);

$^{13}$C NMR (CDCl$_3$): δ159.3, 130.6, 129.4, 113.9, 79.5, 71.2, 64.3, 63.3, 55.3, 32.9, 30.8, 29.8, 29.63, 29.62, 29.60, 29.60, 29.56, 29.4, 26.0, 25.8, 25.4, 18.4, −5.26;
HR MS: calcd for C$_{28}$H$_{52}$O$_4$SiNa (M+Na$^+$) 503.3527. found 503.3503.

(Step 3)

To a solution of the compound B (14.3 mg, 0.030 mmol) in N,N-dimethylformamide (0.15 mL) was added imidazole (8.1 mg, 0.119 mmol), and the reaction system was cooled to 0° C. Thereto was added tert-butyldiphenyl chlorosilane (15.3 μL), and the temperature of the reaction system was elevated to room temperature, followed by stirring the same for 15 min. To the reaction system was added a saturated aqueous ammonium chloride solution to stop the reaction. Diethyl ether was added and liquid separation was carried out. Extraction from the aqueous layer was repeated three times with diethyl ether. Filtration, and vacuum concentration gave a crude product. Thus obtained crude product was purified on thin layer chromatography (developing solvent: hexane/ethyl acetate=5/1) to afford a compound C (19.0 mg, 89%) represented by the following formula as a colorless oily liquid. The physical properties were as in the following.

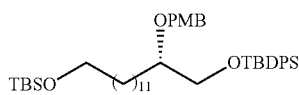

C

[α]$_D^{23}$=−14.5 (c 0.800, benzene);
IR (neat): 3071, 2928, 2855 cm$^{-1}$;
$^1$H NMR (CDCl$_3$): δ7.70-7.67 (m, 4H, TBDPS), 7.45-7.34 (m, 6H, TBDPS), 7.23 (d, J=8.9 Hz, 2H, PMP), 6.85 (d, J=8.9 Hz, 2H, PMP), 4.60 (d, J=11.3 Hz, 1H, PMB), 4.44 (d, J=11.1 Hz, 1H, PMB), 3.80 (s, 3H, OMe), 3.73 (dd, J=10.5, 5.7 Hz, 1H, 1-H), 3.65-3.53 (m, 1H, 1-H), 3.60 (t, J=4.1 Hz, 2H, 14-H), 3.50-3.42 (m, 1H, 2-H), 1.56-1.48 (m, 5H), 1.39-1.12 (m, 17H), 1.06 (s, TBDPS, 9H), 0.90 (s, 9H, TBS), 0.05 (s, 6H, TBS);
$^{13}$C NMR (CDCl$_3$): δ160.9 (PMP), 135.6, 133.7, 131.0, 129.6, 129.3, 127.6, 113.7, 79.5, 71.8, 66.0, 63.4, 55.3, 32.9, 31.7, 29.6, 29.5, 26.8, 26.0, 25.8, 25.3, 19.5, 18.4, −5.3;
HR MS (FAB): calcd for C$_{44}$H$_{70}$O$_4$Si$_2$ (M+H$^+$) 718.4813. found 718.4709.

(Step 4)

A solution of the compound C (6.07 g, 8.44 mmol) in tetrahydrofuran (168 mL) was cooled to 0° C., and thereto was added hydrochloric acid (1.0 M, 42.2 mL, 42.2 mmol). The temperature of the reaction system was elevated to room temperature, followed by stirring the same for 7 hrs. The reaction system was cooled to 0° C., and thereto was added a saturated aqueous sodium bicarbonate solution to stop the reaction. Diethyl ether was added and liquid separation was carried out. Extraction from the aqueous layer was repeated two times with diethyl ether. Organic layers were combined, and washed with water and saturated saline. After the mixture was dried over anhydrous sodium sulfate, filtration and vacuum concentration gave a crude product. Thus obtained crude product was purified on silica gel column chromatography (developing solvent: hexane/ethyl acetate=3/1) to afford a compound D (4.88 g, 96%) represented by the following formula as a colorless oily liquid. The physical properties were as in the following.

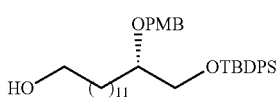

D $[\alpha]_D^{23}$=−16.5 (c 1.00, benzene);

IR (neat): 3374 cm$^{-1}$;

$^1$H NMR (CDCl$_3$): δ7.72-7.64 (m, 4H, TBDPS), 7.40-7.32 (m, 6H, TBDPS), 7.26-7.17 (m, 2H, PMP), 6.87-6.81 (m, 2H, PMP), 4.60 (d, J=11.3 Hz, 1H, PMB), 4.44 (d, J=11.1 Hz, 1H, PMB), 3.80 (s, 3H, OMe), 3.73 (dd, J=10.5, 5.9 Hz, 1H, 1-H), 3.68-3.60 (m, 3H, 1-H, 14-H), 3.53-3.43 (m, 1H, 2-H), 1.66-1.18 (m, 23H), 1.11 (s, 9H, TBDPS);

$^{13}$C NMR (CDCl$_3$): δ160.9, 135.6, 133.7, 131.0, 129.6, 129.3, 127.6, 113.7, 79.5, 71.8, 66.0, 63.1, 55.3, 32.8, 31.7, 29.7, 29.6, 29.4, 26.8, 25.7, 25.4, 19.4;

HR MS (FAB): calcd for C$_{38}$H$_{56}$O$_4$Si (M+H$^+$) 604.3948. found 604.3848.

(Step 5)

A solution of the compound D (3.34 g, 5.53 mmol) in benzene (27.5 mL) was cooled to 0° C., and thereto were added imidazole (941 mg, 13.8 mmol) and triphenylphosphine (3.63 g, 13.8 mmol). Thereafter, iodine (2.82 g, 11.1 mmol) was further added, the temperature of the reaction system was elevated to room temperature, followed by stirring the same for 30 min. The reaction system was cooled to 0° C., and thereto was added a saturated aqueous sodium sulfite solution to stop the reaction. Diethyl ether was added and liquid separation was carried out. Extraction from the aqueous layer was repeated two times with diethyl ether. Organic layers were combined, and washed with water and saturated saline. After the mixture was dried over anhydrous sodium sulfate, filtration and vacuum concentration gave a crude product. Thus obtained crude product was purified on silica gel column chromatography (developing solvent: hexane/ethyl acetate=20/1) to afford a compound E (3.59 g, 91%) represented by the following formula as a colorless oily liquid. The physical properties were as in the following.

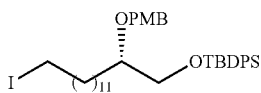

E $[\alpha]_D^{21}$=−6.61 (c 0.947, benzene);

IR (neat): 3070, 3048, 2998, 2927, 2854 cm$^{-1}$;

$^1$H NMR (CDCl$_3$): δ7.71-7.63 (m, 4H, TBDPS), 7.46-7.33 (m, 6H, TBDPS), 7.26-7.23 (m, 2H, PMP), 6.88-6.84 (m, 2H, PMP), 4.61 (d, J=11.3 Hz, 1H, PMB), 4.44 (d, J=11.1 Hz, 1H, PMB), 3.80 (s, 3H, OMe), 3.73 (dd, J=10.5, 5.9 Hz, 1H, 1-H), 3.63 (dd, J=10.5, 4.6 Hz, 1H, 1-H), 3.53-3.43 (m, 1H, 2-H), 3.19 (t, J=7.0 Hz, 2H, 14-H), 1.82 (d, t, J=14.3, 7.0 Hz, 2H), 1.60-1.18 (m, 20H), 1.07 (s, 9H, TBS);

$^{13}$C NMR (CDCl$_3$): δ160.9, 135.6, 133.6, 131.2, 129.6, 129.3, 127.6, 113.6, 79.4, 71.8, 66.4, 55.3, 33.6, 31.6, 30.5, 29.7, 29.6, 29.4, 28.5, 26.8, 25.4, 19.2, 7.4;

HR MS (FAB): calcd for C$_{38}$H$_{55}$O$_3$Si (M+H$^+$) 714.2965. found 714.2864.

(Step 6)

To copper iodide (285 mg, 1.50 mmol) which had been dried beforehand by heating under a reduced pressure was added a solution of 2,2'-bipyridyl (235 mg, 1.50 mmol) in tetrahydrofuran (1.1 mL). Further, a solution of the compound E (3.57 g, 5.00 mmol) in tetrahydrofuran (10.0 mL) was added thereto. The reaction system was cooled to −17° C. and stirred for 15 min. Subsequently, a separately prepared Grignard reagent (0.555 M tetrahydrofuran solution, 18.4 mL, 10.2 mmol) was added thereto. The temperature of the reaction system was elevated to room temperature, followed by stirring the same for 1 hour. The reaction system was cooled to 0° C., and a saturated aqueous ammonium chloride solution was added thereto to stop the reaction. After diethyl ether was added, Celite was used to filtrate insoluble matter off. Liquid separation was carried out, and extraction from the aqueous layer was repeated two times with diethyl ether. Organic layers were combined, washed with water and saturated saline. After the mixture was dried over anhydrous sodium sulfate, filtration and vacuum concentration gave a crude product. Thus obtained crude product was purified on silica gel column chromatography (developing solvent: hexane/ethyl acetate=40/1) to afford a compound F (4.10 g, 96%) represented by the following formula as a colorless oily liquid. The physical properties were as in the following.

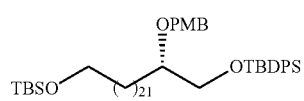

F $[\alpha]_D^{21}$=−12.1 (c 1.01, benzene);

IR (neat): 3071, 3049, 2999, 2926, 2854 cm$^{-1}$;

$^1$H NMR (CDCl$_3$): δ7.72-7.65 (m, 4H, TBDPS), 7.46-7.35 (m, 6H, TBDPS), 7.26-7.23 (m, 2H, PMP), 6.88-6.84 (m, 2H, PMP), 4.61 (d, J=11.3 Hz, 1H, PMB), 4.45 (d, J=11.3 Hz, 1H, PMB), 3.81 (s, 3H, OMe), 3.74 (dd, J=10.5, 5.9 Hz, 1H, 1-H), 3.63 (dd, J=10.5, 4.6 Hz, 1H, 1-H), 3.61 (t, J=6.8 Hz, 2H, 24-H), 3.54-3.43 (m, 1H, 2-H), 1.63-1.49 (m, 4H), 1.37-1.19 (m, 38H), 1.08 (s, 9H, TBDPS), 0.91 (s, 9H, TBS), 0.06 (s, 6H, TBS);

$^{13}$C NMR (CDCl$_3$): δ159.0, 135.6, 133.6, 131.2, 129.6, 129.3, 127.6, 113.6, 79.4, 71.8, 66.3, 63.3, 55.2, 32.8, 31.6, 29.7, 29.6, 29.4, 26.8, 26.0, 25.8, 25.4, 19.2, 18.4, −5.3;

HR MS (ESI TOF): calcd for C$_{54}$H$_{90}$O$_4$Si$_2$Na (M+Na$^+$) 881.6270. found 881.6249.

(Step 7)

A solution of the compound F (1.65 g, 1.92 mmol) in tetrahydrofuran (96 mL) was cooled to 0° C., and thereto was added hydrochloric acid (1.0 M, 9.6 mL, 9.56 mmol). The temperature of the reaction system was elevated to room temperature, followed by stirring the same for 2.5 hrs. The reaction system was cooled to 0° C., and thereto was added a saturated aqueous sodium bicarbonate solution to stop the reaction. Diethyl ether was added and liquid separation was carried out. Extraction from the aqueous layer was repeated two times with diethyl ether. Organic layers were combined, and washed with water and saturated saline. After the mixture was dried over anhydrous sodium sulfate, filtration and vacuum concentration gave a crude product. Thus obtained crude product was purified on silica gel column chromatography (developing solvent: benzene/ethyl acetate/methanol=30/1/1) to afford a compound G (1.34 g, 94%) represented by the following formula as a colorless oily liquid. The physical properties were as in the following.

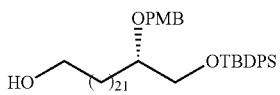

G

[α]$_D^{27}$=−9.90 (c 1.03, benzene);
IR (neat): 3357 cm$^{-1}$;
$^1$H NMR (CDCl$_3$): δ7.75-7.72 (m, 4H), 7.51-7.35 (m, 6H), 7.29-7.26 (m, 2H), 6.90-6.87 (m, 2H), 4.64 (d, J=11.3 Hz, 1H), 4.48 (d, J=11.3 Hz, 1H), 3.82 (s, 3H), 3.81-3.61 (m, 2H, 1-H), 3.65 (t, J=6.6 Hz, 2H, 24-H), 3.56-3.46 (m, 1H, 2-H), 1.65-1.18 (m, 42H), 1.11 (s, 9H);
$^{13}$C NMR (CDCl$_3$): δ159.0, 135.6, 133.6, 131.1, 129.6, 129.3, 127.6, 113.6, 79.4, 71.7, 66.3, 63.0, 55.2, 32.7, 31.6, 29.7, 29.6, 29.4, 26.8, 25.7, 25.3, 19.2;
HR MS (ESI TOF): calcd for C$_{48}$H$_{76}$O$_4$SiNa (M+Na$^+$) 767.5405. found 767.5406.

(Step 8)

To a solution of the compound G (3.08 g, 4.13 mmol) in methylene chloride (41.2 mL) was added pyridinium chlorochromate (1.34 g, 6.20 mmol), and the mixture was stirred for 11 hrs. The reaction system was diluted by adding diethyl ether. Gravity filtration, and vacuum concentration gave a crude product. Thus obtained crude product was purified on silica gel column chromatography (developing solvent: hexane/ethyl acetate=10/1) to afford a compound H (2.52 g, 82%) represented by the following formula as a colorless oily liquid. The physical properties were as in the following.

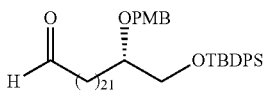

H

[α]$_D^{22}$=−14.3 (c 1.03, benzene);
IR (neat): 1727 cm$^{-1}$;
$^1$H NMR (CDCl$_3$): δ9.76 (s, 1H, CHO), 7.70-7.67 (m, 4H, TBDPS), 7.45-7.34 (m, 6H, TBDPS), 7.23 (d, J=8.7 Hz, 2H, PMP), 6.85 (d, J=9.0 Hz, 2H, PMP), 4.60 (d, J=11.4 Hz, 1H, PMB), 4.44 (d, J=11.4 Hz, 1H), 3.80 (s, 3H, PMB), 3.73 (dd, J=11.9, 5.9 Hz, 1H, 1-H), 3.62 (dd, J=10.8, 4.8 Hz, 1H, 1-H), 3.50-3.44 (m, 1H, 2-H), 2.42 (t, d, J=7.4, 1.8 Hz, 2H, 23-H), 1.65-1.44 (m, 4H, 3-H, 22-H), 1.35-1.18 (m, 38H, 4-H to 21-H), 1.06 (s, 9H, TBDPS);
$^{13}$C NMR (CDCl$_3$): δ203.0, 159.0, 135.6, 133.6, 131.2, 129.6, 129.3, 127.6, 113.6, 79.4, 71.7, 66.4, 55.2, 43.9, 31.6, 29.70, 29.63, 29.59, 29.41, 29.34, 29.14, 26.8, 25.4, 22.1, 19.2;
HR MS (ESI TOF): calcd for C$_{48}$H$_{74}$O$_4$SiNa (M+Na$^+$) 765.5249. found 765.5270.

(Step 9)

A solution of the compound H (2.52 g, 3.40 mmol) in tetrahydrofuran (7.6 mL) was cooled to 0° C., and a separately prepared Grignard reagent (0.686 M, 9.9 mL, 6.81 mmol) was added thereto, followed by stirring the mixture for 2 hrs. A saturated aqueous ammonium chloride solution was added to the reaction system to stop the reaction. Diethyl ether was added and liquid separation was carried out. Extraction from the aqueous layer was repeated two times with diethyl ether. Organic layers were combined, and washed with water and saturated saline. After the mixture was dried over anhydrous sodium sulfate, filtration and vacuum concentration gave a crude product. Thus obtained crude product was purified on silica gel column chromatography (developing solvent: hexane/ethyl acetate=5/1) to afford a compound I (2.70 g, 88%) represented by the following formula as a colorless oily liquid. The physical properties were as in the following.

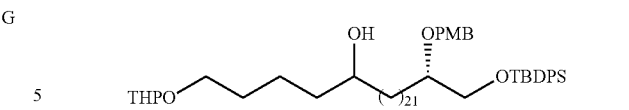

I

IR (neat): 3448 cm$^{-1}$;
$^1$H NMR (CDCl$_3$): δ7.78-7.64 (m, 4H, TBDPS), 7.47-7.33 (m, 6H, TBDPS), 7.28-7.20 (m, 2H, PMP), 6.89-6.81 (m, 2H, PMP), 4.61 (d, J=11.1 Hz, 1H, PMB), 4.59 (s, 1H, THP), 4.45 (d, J=11.1 Hz, 1H, PMB), 3.93-3.36 (m, 8H, 1-H, 2-H, 24-H, 28-H, THP), 3.80 (s, 3H, OMe), 1.89-1.15 (m, 54H);
$^{13}$C NMR (CDCl$_3$): δ159.0, 135.6, 133.6, 131.2, 129.6, 129.3, 127.6, 113.6, 98.9, 79.4, 71.7, 67.5, 66.4, 64.3, 62.3, 55.2, 37.5, 37.1, 31.6, 30.7, 29.7, 29.6, 26.8, 25.6, 25.3, 22.3, 19.6, 19.2;
HR MS (ESI TOF): calcd for C$_{57}$H$_{92}$O$_6$SiNa (M+Na$^+$) 923.6555. found 923.6554.

(Step 10)

A solution of the compound I (1.38 g, 1.53 mmol) in methylene chloride (5 mL) was cooled to 0° C., and thereto were added dihydropyran (0.2 mL, 2.19 mmol) and p-toluenesulfonic acid monohydrate (32.7 mg, 0.190 mmol). The temperature of the reaction system was elevated to room temperature, followed by stirring the same for 2 hrs. The reaction system was cooled to 0° C., and thereto was added a saturated aqueous sodium bicarbonate solution to stop the reaction. Methylene chloride was added and liquid separation was carried out. Extraction from the aqueous layer was repeated two times with methylene chloride. Organic layers were combined, and washed with water and saturated saline. After the mixture was dried over anhydrous sodium sulfate, filtration and vacuum concentration gave a crude product. Thus obtained crude product was purified on silica gel column chromatography (developing solvent: hexane/ethyl acetate=15/1) to afford a compound J (1.30 g, 86%) represented by the following formula as a colorless oily liquid. The physical properties were as in the following.

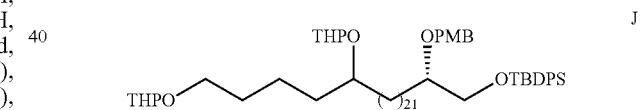

J

IR (neat): 3070, 3044, 2924, 2853 cm$^{-1}$;
$^1$H NMR (CDCl$_3$): δ7.71-7.67 (m, 4H, TBDPS), 7.47-7.35 (m, 6H, TBDPS), 7.26-7.17 (m, 2H, PMP), 6.88-6.80 (m, 2H, PMP), 4.60 (d, J=11.1 Hz, 1H, PMB), 4.58 (s, 1H, THP), 4.44 (d, J=11.3 Hz, 1H, PMB), 3.92-3.32 (m, 8H, 1-H, 2-H, 24-H, 28-H, THP), 3.80 (s, 3H, OMe), 1.88-1.11 (m, 54H), 1.07 (s, 9H, TBDPS);
$^{13}$C NMR (CDCl$_3$): δ158.9, 135.6, 133.6, 131.1, 129.6, 129.3, 127.6, 113.6, 100.5, 95.4, 79.4, 71.8, 67.5, 66.4, 62.7, 62.2, 62.1, 55.3, 35.0, 34.8, 30.8, 30.7, 29.9, 29.5, 26.8, 25.5, 25.0, 22.3, 20.0, 19.7, 19.6;
HR MS (ESI TOF): calcd for C$_{62}$H$_{100}$O$_7$SiNa (M+Na$^+$) 1007.7131. found 1007.7123.

(Step 11)

A solution of the compound J (654.6 mg, 0.664 mmol) in tetrahydrofuran (7.2 mL) was cooled to 0° C., and tetrabutylammonium fluoride (1.0 M tetrahydrofuran solution, 2.0 mL, 2.0 mmol) was added thereto. To the reaction system was added acetic acid (0.12 mL, 2.10 mmol), and the temperature was elevated to room temperature, followed by stirring the same for 22.5 hrs. The reaction system was cooled to 0° C., and thereto was added a saturated aqueous sodium bicarbonate solution to stop the reaction, Ethyl acetate was added and liquid separation was carried out. Extraction from the aqueous layer was repeated two times with ethyl acetate. Organic layers were combined, and washed with water and saturated saline. After the mixture was dried over anhydrous sodium sulfate, filtration and vacuum concentration gave a crude product. Thus obtained crude product was purified on silica gel column chromatography (developing solvent: hexane/ethyl acetate=3/1) to afford a compound K (474 mg, 96%) represented by the following formula as a colorless oily liquid. The physical properties were as in the following.

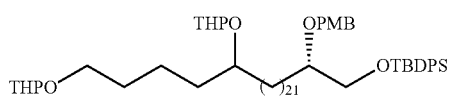

IR (neat): 3466 cm$^{-1}$;

$^1$H NMR (CDCl$_3$): δ7.27 (d, J=8.4 Hz, 2H, PMP), 6.91-6.86 (m, 2H, PMP), 4.67-4.62 (m, 1H, THP), 4.60-4.55 (m, 1H, THP), 4.56 (d, J=11.3 Hz, 1H, PMB), 4.46 (d, J=11.1 Hz, 1H, PMB), 3.95-3.34 (m, 10H, 1-H, 2-H, 24-H, 28-H, THP), 3.81 (s, 3H, OMe), 1.86-1.38 (m, 20H, 3-H, 23-H, 25-H, 27-H, THP), 1.38-1.16 (m, 40H);

$^{13}$C NMR (CDCl$_3$): δ159.2, 130.6, 129.3, 113.8, 98.8, 97.6, 79.4, 71.1, 67.5, 64.3, 62.7, 62.3, 62.2, 55.3, 35.0, 34.8, 30.8, 30.7, 29.9, 29.5, 25.5, 25.0, 22.3, 20.0, 19.6;

HR MS (ESI TOF): calcd for C$_{46}$H$_{82}$O$_7$Na (M+Na$^+$) 769.5953. found 769.5953.

(Step 12)

To a solution of the compound K (588.1 mg, 0.787 mmol) in acetonitrile (3.9 mL) were added 2,2,6,6-tetramethylpiperidine 1-oxyl (18.0 mg, 0.115 mmol) and a buffered solution (2.95 mL). The temperature of the reaction system was elevated to an external temperature of 35° C., and an aqueous sodium hypochlorite solution (2.0 M, 1.58 mL, 3.15 mmol) and an aqueous sodium hypochlorite solution (5% NaOCl 0.1 mL/water 1.89 mL, 0.4 mL, 31.5 μmol) were added thereto. The reaction system was confirmed to be weekly acidic with a pH test paper, and stirred for 8.5 hrs. The temperature of the reaction system was elevated to room temperature, and water (5.9 mL) was added thereto. Thereafter, the reaction system was cooled to 0° C., and thereto was added a 6% aqueous sodium sulfite solution to stop the reaction. Diethyl ether was added and liquid separation was carried out. Extraction from the aqueous layer was repeated two times with diethyl ether. Organic layers were combined, and washed with water and saturated saline. After the mixture was dried over anhydrous sodium sulfate, filtration and vacuum concentration gave a crude product of a compound L (599 mg, quant.) represented by the following formula. Thus obtained crude product was used in the next step without subjecting to purification.

It is to be noted that thus obtained crude product was purified on silica gel column chromatography (developing solvent: trichloromethane/methanol=10/1) to afford the compound L as a white solid, which was then analyzed by NMR. The physical properties were as in the following.

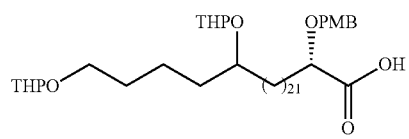

IR (neat): 3446, 1700 cm$^{-1}$;

$^1$H NMR (CDCl$_3$): δ7.27 (d, J=8.7 Hz, 2H, PMP), 6.89 (d, J=8.7 Hz, 2H, PMP), 4.58 (s, 2H, THP), 4.55 (d, J=11.3 Hz, 1H, PMB), 4.47 (d, J=11.1 Hz, 1H, PMB), 3.93-3.34 (m, 8H, 2-H, 24-H, 28-H, THP), 3.80 (s, 3H, OMe), 1.95-1.16 (m, 60H);

HR MS (ESI TOF): calcd for C$_{46}$H$_{80}$O$_8$Na (M+Na$^+$) 783.5745. found 783.5739.

(Step 13)

A solution of the compound L (599 mg, 0.787 mmol) in tetrahydrofuran (40 mL) was cooled to 0° C., and hydrochloric acid (1.0 M, 4.0 mL, 4.0 mmol) was added thereto. The temperature of the reaction system was elevated to room temperature, followed by stirring the same for 71 hrs. The reaction system was cooled to 0° C., and thereto was added a saturated aqueous sodium bicarbonate solution to stop the reaction. Ethyl acetate was added and liquid separation was carried out. Extraction from the aqueous layer was repeated two times with ethyl acetate. Organic layers were combined, and washed with water and saturated saline. After the mixture was dried over anhydrous sodium sulfate, filtration and vacuum concentration gave a crude product. Thus obtained crude product was purified on silica gel column chromatography (developing solvent: dichloromethane/methanol=20/1) to afford a compound M (262 mg, 56%, 2 steps) represented by the following formula as a white solid. The physical properties were as in the following.

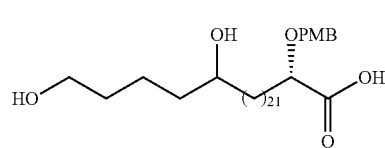

Mp: 62-63° C.;

IR (neat): 3416, 1716 cm$^{-1}$;

$^1$H NMR (CDCl$_3$): δ7.29-7.26 (m, 2H, PMP), 6.92-6.87 (m, 2H, PMP), 4.60 (d, J=11.4 Hz, 1H, PMB), 4.46 (d, J=11.4 Hz, 1H, PMB), 3.98 (t, J=5.9 Hz, 1H, 2-H), 3.81 (s, 3H, OMe), 3.67 (t, J=6.3 Hz, 2H, 28-H), 3.61 (m, 1H, 24-H), 1.82-1.72 (m, 2H), 1.61-1.25 (m, 48H);

$^{13}$C NMR (CDCl$_3$): δ174.7, 159.3, 129.8, 129.0, 113.9, 72.3, 72.0, 70.0, 62.8, 55.3, 37.5, 36.9, 32.5, 32.3, 29.6, 29.4, 29.2, 25.6, 24.8, 21.8;

HR MS (ESI TOF): calcd for C$_{36}$H$_{64}$O$_6$Na (M+Na$^+$) 615.4595. found 615.4597.

(Step 14)

To a solution of 2-methyl-6-nitrobenzoic acid anhydride (24.8 mg, 72.0 μmol) in methylene chloride (9.6 mL) were added 4-dimethylaminopyridine N-oxide (1.7 mg, 12.3 μmol) and triethylamine (0.02 mL, 0.161 mmol), and the mixture was heated to reflux at an external temperature of 50° C. A solution of seco acid M (31.8 mg, 53.6 μmol) in tetrahydrofuran (16.3 mL) was added dropwise into the reaction system using a syringe pump over 12 hrs. After completing the dropwise addition, a solution of tetrahydrofuran (1.0 mL) was used for rinsing, and the mixture was stirred at 50° C. for 1 hour. The reaction system was cooled to 0° C., and thereto was added a saturated aqueous sodium bicarbonate solution to stop the reaction. Methylene chloride was added and liquid separation was carried out. Extraction from the aqueous layer was repeated two times with methylene chloride. Organic layers were combined, and washed with water and saturated saline. After the mixture was dried over anhydrous sodium sulfate, filtration and vacuum concentration gave a crude product. Thus obtained crude product was purified on silica gel thin layer chromatography (developing solvent: hexane/ethyl acetate=3/1) to afford a compound N (23.6 mg, 77%) represented by the following formula as a colorless oily liquid. The physical properties were as in the following.

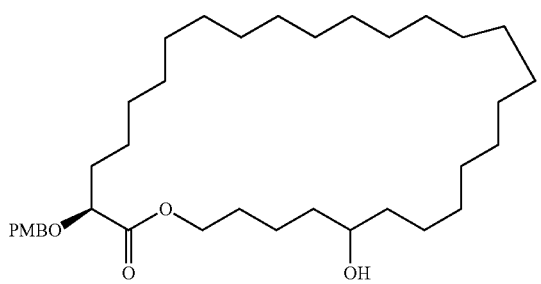

IR (neat): 3446, 1636 cm$^{-1}$;

$^1$H NMR (CDCl$_3$): δ7.28 (d, J=8.5 Hz, 2H, PMP), 6.88 (d, J=8.5 Hz, 2H, PMP), 4.63 (d, J=11.0 Hz, 1H, PMB), 4.34 (d, J=11.0 Hz, 1H, PMB), 4.22-4.18 (m, 1H, 28-H), 4.16-4.09 (m, 1H, 28-H), 3.90 (t, J=6.5 Hz, 1H, 2-H), 3.80 (s, 3H, OMe), 3.66-3.55 (m, 1H, 24-H), 1.76-1.26 (m, 48H);

$^{13}$C NMR (CDCl$_3$): δ174.0, 159.3, 131.9, 129.7, 113.7, 77.4, 71.8, 71.6, 64.7, 55.3, 37.3, 36.8, 33.0, 29.35, 29.25, 29.17, 29.10, 29.03, 28.90, 28.86, 28.75, 28.66, 28.61, 28.56, 25.4, 25.3, 25.0, 22.1;

HR MS (ESI TOF): calcd for C$_{36}$H$_{62}$O$_5$Na (M+Na$^+$) 597.4489. found 597.4489.

(Step 15)

A solution of the compound N (60.1 mg, 0.105 mmol) in methylene chloride (1.0 mL) was added to molecular sieves 4 Å (62.7 mg) which had been heated beforehand to dry under a reduced pressure. Thereto was added N-methylmorpholine N-oxide (36.7 mg, 0.314 mmol), and the reaction system was cooled to 0° C. Tetrapropylammonium perruthenate (7.4 mg, 20.9 μmol) was added thereto, and the mixture was stirred for 4.5 hrs. After completing the reaction, filtration was carried out using silica gel (developing solvent: hexane/ethyl acetate=3/1), and vacuum concentration gave a crude product (59.9 mg, quant.) of a compound O represented by the following formula. Thus obtained crude product was used in the next step without subjecting to purification.

It is to be noted that thus obtained crude product was purified on silica gel thin layer chromatography (developing solvent: hexane/ethyl acetate=3/1) to afford the compound O as a white solid, which was then analyzed by NMR. The physical properties were as in the following.

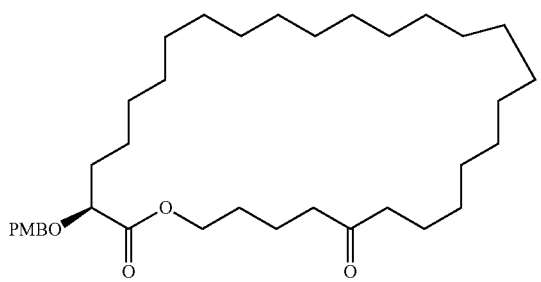

$[\alpha]_D^{22}$=−34.4 (c 0.753, benzene);
IR (neat): 1737, 1712 cm$^{-1}$;

$^1$H NMR (CDCl$_3$): δ7.30-7.26 (m, 2H, PMP), 6.90-6.84 (m, 2H, PMP), 4.62 (d, J=11.1 Hz, 1H, PMB), 4.33 (d, J=11.3 Hz, 1H, PMB), 4.20-4.07 (m, 2H, 28-H), 3.89 (t, J=6.5 Hz, 1H, 2-H), 3.80 (s, 3H, OMe), 2.45 (t, J=7.0 Hz, 2H, 25-H), 2.38 (t, J=7.4 Hz, 2H, 23-H), 1.78-1.50 (m, 10H), 1.45-1.18 (m, 34H);

$^{13}$C NMR (CDCl$_3$): δ210.8, 173.0, 159.3, 132.7, 129.7, 113.3, 71.9, 64.4, 55.3, 42.8, 42.0, 33.0, 29.32, 29.23, 29.18, 29.09, 28.98, 28.78, 28.72, 28.64, 28.59, 28.2, 25.2, 23.8, 20.3;

HR MS (ESI TOF): calcd for C$_{36}$H$_{60}$O$_5$Na (M+Na$^+$) 595.4333, found 595.4333.

(Step 16)

To a solution of the compound O (59.9 mg, 0.105 mmol) in methylene chloride (2.0 mL) was added water (0.2 mL), and cooled to 0° C. Thereto was added 2,3-dichloro-5,6-dicyano-1,4-benzoquinone (28.5 mg, 0.126 mmol), and the temperature of the reaction system was elevated to room temperature, followed by stirring the same for 38.5 hrs. The reaction system was cooled to 0° C., and thereto was added a buffered solution to stop the reaction. Methylene chloride was added and liquid separation was carried out. Extraction from the aqueous layer was repeated two times with methylene chloride. Organic layers were combined, and washed with water and saturated saline. After the mixture was dried over anhydrous sodium sulfate, filtration and vacuum concentration gave a crude product. Thus obtained crude product was purified on silica gel thin layer chromatography (developing solvent: benzene/diethyl ether=3/1) to afford 2-hydroxy-24-oxooctacosanolide intended (40.8 mg, 86%, 2 steps) represented by the following formula as a white solid. The physical properties were as in the following.

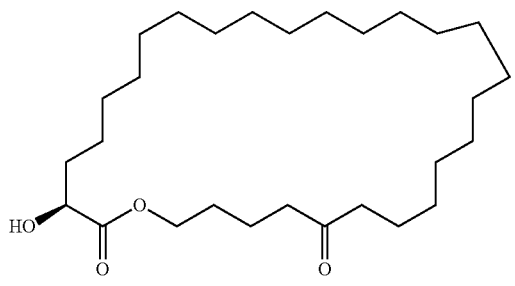

2-Hydroxy-24-oxooctacosanolide

Mp: 67-68° C.;
$[\alpha]_D^{21}$=−9.6 (c 0.96, benzene);
IR (neat): 3445, 1739, 1713 cm$^{-1}$;

$^1$H NMR (CDCl$_3$): δ4.28-4.24 (m, 1H, 28-H), 4.18-4.16 (m, 1H, 2-H), 4.13-4.09 (m, 1H, 28-H), 2.45 (t, J=7.0 Hz, 2H, 25-H), 2.40 (t, J=7.5 Hz, 2H, 23-H), 1.81-1.75 (m, 2H, 3-H), 1.69-1.63 (m, 2H, 27-H), 1.67-1.61 (m, 2H, 26-H), 1.61-1.56 (m, 2H, 22-H), 1.56-1.45 (m, 2H, 4-H), 1.45-1.17 (m, 34H, 5-H to 21-H);

$^{13}$C NMR (CDCl$_3$): δ210.7, 175.6, 70.4, 65.4, 42.8, 42.0, 34.4, 29.40, 29.29, 29.27, 29.20, 29.12, 28.98, 28.92, 28.89, 28.81, 28.74, 28.72, 28.67, 28.60, 28.58, 28.50, 28.1, 24.7, 23.7, 20.2;

HR MS (ESI TOF): calcd for C$_{28}$H$_{52}$O$_4$Na (M+Na$^+$) 475.3758. found 475.3758.

Test Example 8

Production of Optically Active Amino Alcohol Using Optically Active Hydroxy Ester The optically active hydroxy ester obtained according to the production method of the present invention is useful also in producing an optically active amino alcohol. One example of the method for producing an optically active amino alcohol is shown below.

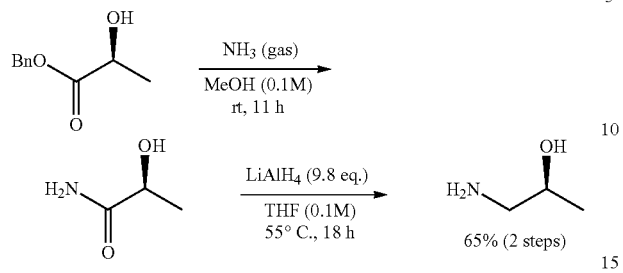

As shown in the above reaction scheme, ammonia gas was bubbled into a solution of benzyl (S)-lactate ester (45.2 mg, 0.251 mmol) in methanol (2.50 mL) at 0° C. for 70 min. After the reaction mixture was stirred at room temperature for 11 hrs, concentration gave a crude product of corresponding amide.

Subsequently, to a solution of thus obtained crude amide product in tetrahydrofuran (2.50 mL) was added lithium aluminium hydride (92.6 mg, 2.47 mmol) at 0° C. The reaction mixture was stirred at room temperature for 10 min, and the temperature was elevated to 55° C., followed by stirring the same for 18 hrs. Thereafter, water (200 μL) was added at 0° C. to stop the reaction. The reaction mixture was filtrated through Celite, and subjected to vacuum concentration. Thereafter, fractionation was carried out on silica gel thin layer chromatography (developing solvent: chloroform saturated with ammonia by aqueous ammonia extraction/methanol=50/1) to afford corresponding optically active amino alcohol (14.5 mg, 65%). The physical properties were as in the following.

$[\alpha]_D^{22}$=+44.4 (c 1.0, methanol);
$^1$H NMR (CDCl$_3$): δ3.65-2.55 (m, 1H), 3.80-2.40 (br m, 3H), 2.65 (dd, J=12.7, 2.7 Hz, 1H), 2.44 (dd, J=12.7, 8.1 Hz, 1H), 1.06 (d, J=6.3 Hz, 3H).

The invention claimed is:

1. A method for producing an optically active 2-hydroxy ester, the method comprising selectively esterifying one enantiomer of a racemic 2-hydroxy ester in a solvent containing a catalyst represented by any one of the following formulae (a) to (d), and a carboxylic acid anhydride, or a carboxylic acid anhydride and a carboxylic acid, the racemic 2-hydroxy ester being a compound represented by formula (f) below,
the carboxylic acid anhydride being an anhydride of a carboxylic acid having a tertiary carbon atom or a quaternary carbon atom in the α-position, provided that the solvent contains a carboxylic acid anhydride but does not contain a carboxylic acid, whereas
the carboxylic acid has a tertiary carbon atom or a quaternary carbon atom in the α-position, provided that the solvent contains a carboxylic acid anhydride and a carboxylic acid,

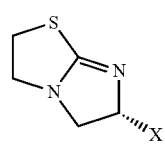

(a)

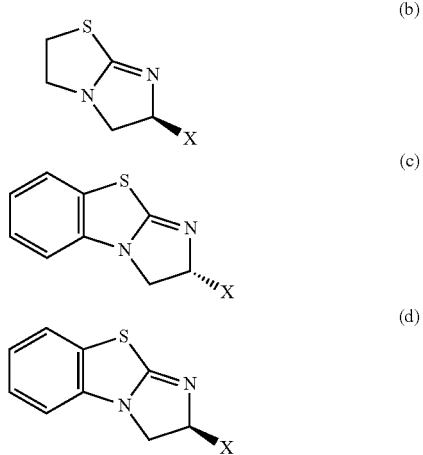

wherein, X represents any one of the following substituents:

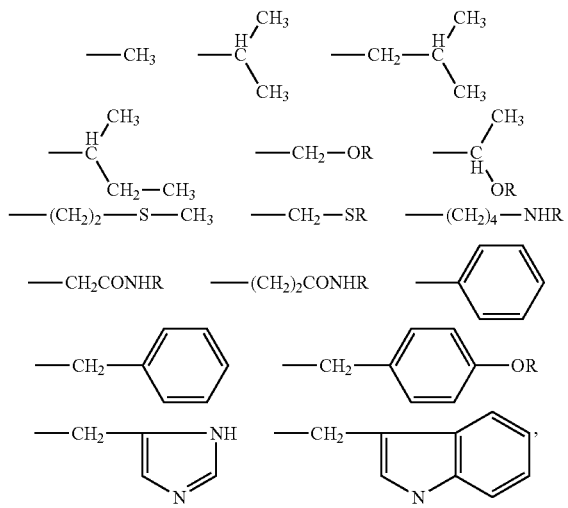

and R represents a protecting group,

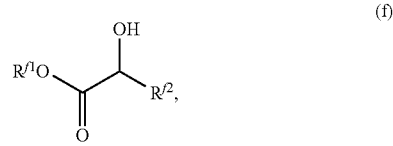

wherein, R$^{f1}$ represents a monovalent organic group, and R$^{f2}$ represents a group selected from the group consisting of alkyl group, cycloalkyl group, alkenyl group, cycloalkenyl group, alkynyl group, and arylalkyl group.

2. The method for producing an optically active 2-hydroxy ester according to claim 1, wherein the one enantiomer of the racemic 2-hydroxy ester is selectively esterified in a solvent comprising diphenylacetic acid anhydride as the carboxylic acid anhydride.

3. The method for producing an optically active 2-hydroxy ester according to claim 1, wherein the one enantiomer of the racemic 2-hydroxy ester is selectively esterified in a solvent comprising pivalic acid anhydride as the carboxylic acid anhydride, and diphenylacetic acid as the carboxylic acid.

4. The method for producing an optically active 2-hydroxy ester according to claim 1, wherein the solvent is a linear ether type solvent.

\* \* \* \* \*